(12) United States Patent
Bert et al.

(10) Patent No.: US 9,486,649 B2
(45) Date of Patent: Nov. 8, 2016

(54) METHOD AND IRRADIATION INSTALLATION FOR IRRADIATING A TARGET VOLUME

(71) Applicant: GSI Helmholtzzentrum Fur Schwerionenforschung GmbH, Darmstadt (DE)

(72) Inventors: Christoph Bert, Aschaffenburg (DE); Alexander Gemmel, Erlangen (DE); Robert Luechtenborg, Darmstadt (DE)

(73) Assignee: GSI Helmholtzzentrum Fur Schwerionenforschung GmbH, Darmstadt (DE)

( * ) Notice: Subject to any disclaimer, the term of this patent is extended or adjusted under 35 U.S.C. 154(b) by 32 days.

(21) Appl. No.: 14/383,306

(22) PCT Filed: Mar. 5, 2013

(86) PCT No.: PCT/EP2013/054361
§ 371 (c)(1),
(2) Date: Feb. 9, 2015

(87) PCT Pub. No.: WO2013/131890
PCT Pub. Date: Sep. 12, 2013

(65) Prior Publication Data
US 2015/0217139 A1 Aug. 6, 2015

(30) Foreign Application Priority Data

Mar. 5, 2012 (DE) .................... 10 2012 004 170

(51) Int. Cl.
*A61N 5/10* (2006.01)
*G21K 5/00* (2006.01)

(52) U.S. Cl.
CPC ............. *A61N 5/1067* (2013.01); *A61N 5/107* (2013.01); *A61N 5/1043* (2013.01);
(Continued)

(58) Field of Classification Search
CPC .... A61N 5/10; A61N 5/1043; A61N 5/1048; A61N 5/1049; A61N 5/1067; A61N 5/1077; A61N 5/1081; A61N 5/1038; A61N 5/1039; A61N 5/1064; A61N 5/1065; A61N 5/1069; A61N 5/1079; A61N 5/103; A61N 5/1031; A61N 5/1042; A61N 5/1068; A61N 5/1071; H05H 13/04; H05H 7/10; H05H 7/04; H05H 7/01; A61B 6/032; A61B 6/583; A61B 6/4258; A61B 6/027; A61B 6/06; A61B 6/4085; A61B 6/4405; A61B 6/4458; A61B 6/466; A61B 6/482; A61B 6/508; A61B 6/5205; A61B 6/037; A61B 6/12; A61B 6/14; A61B 6/4216; A61B 6/4266; A61B 6/4494; A61B 6/469; A61B 6/5235; G21K 1/087; G21K 1/093; G21K 1/10; G21K 1/04; G21K 1/046; G21K 5/04; G21K 5/10

USPC ........... 250/492.3, 492.1, 396 R, 505.1, 306, 250/366, 370.01, 370.08, 370.09, 454.11, 250/491.1, 492.21, 515.1; 600/1, 427; 315/503, 504, 501; 378/65, 156, 159, 378/19, 191, 195, 196, 197, 198, 20, 68
See application file for complete search history.

(56) References Cited

U.S. PATENT DOCUMENTS 5,986,274 A * 11/1999 Akiyama .................. A61N 5/10
250/492.1
6,087,672 A * 7/2000 Matsuda .............. A61N 5/1042
250/492.3
(Continued)

FOREIGN PATENT DOCUMENTS

DE  102009055902  6/2011
EP  2229981  9/2010
(Continued)

OTHER PUBLICATIONS

PCT Int Search Report, Int Serial No. PCT/EP2013/054361, Int Filing Date: Mar. 5, 2013, Applicant: GSI Helmholtzzentrum Fur Schwerionenforschung GmbH, Date Mailed: Apr. 19, 2013.
(Continued)

*Primary Examiner* — David A Vanore
(74) *Attorney, Agent, or Firm* — Reising Ethington P.C.; Steven Walmsley

(57) ABSTRACT

The present disclosure relates to a method and to an irradiation system for irradiating a moving target volume with an ion beam, in particular for tumor therapy, wherein ion radiography measurements of the target volume are performed and the irradiation for deposition purposes and for radiography purposes is performed with the same ion beam but consecutively in time by alternating the energy of the ion beam between a higher radiography energy and a lower deposition energy using, for example, a passive energy modulator proximal with respect to the patient.

28 Claims, 14 Drawing Sheets

(52) U.S. Cl.
CPC ............... *A61N 2005/1054* (2013.01); *A61N 2005/1062* (2013.01); *A61N 2005/1087* (2013.01); *A61N 2005/1095* (2013.01)

(56) References Cited

U.S. PATENT DOCUMENTS

| | | | | |
|---|---|---|---|---|
| 6,265,837 | B1* | 7/2001 | Akiyama | A61N 5/1043 250/492.3 |
| 6,683,318 | B1* | 1/2004 | Haberer | A61N 5/10 250/492.3 |
| 7,291,841 | B2* | 11/2007 | Nelson | G01T 1/243 250/370.01 |
| 7,471,765 | B2* | 12/2008 | Jaffray | A61B 6/032 378/196 |
| 7,939,809 | B2* | 5/2011 | Balakin | A61N 5/10 250/396 R |
| 8,109,865 | B2* | 2/2012 | Jackson | A61N 5/10 600/1 |
| 8,421,041 | B2* | 4/2013 | Balakin | G21K 1/087 250/491.1 |
| 9,207,193 | B2* | 12/2015 | Censor | G01N 23/046 |
| 9,220,920 | B2* | 12/2015 | Schulte | A61N 5/1039 |
| 2009/0039256 | A1* | 2/2009 | Fujii | A61N 5/1048 250/306 |
| 2011/0313232 | A1* | 12/2011 | Balakin | A61N 5/10 600/1 |
| 2012/0181437 | A1* | 7/2012 | Nelson | G01T 1/2012 250/366 |
| 2012/0238795 | A1* | 9/2012 | Bert | A61N 5/1043 600/1 |
| 2013/0267756 | A1* | 10/2013 | Totake | A61N 5/1048 600/1 |
| 2015/0031931 | A1* | 1/2015 | Nishiuchi | A61N 5/1067 600/1 |
| 2015/0246244 | A1* | 9/2015 | Sossong | A61N 5/1039 600/427 |

FOREIGN PATENT DOCUMENTS

| | | | |
|---|---|---|---|
| EP | 1871477 B1 | 3/2011 | |
| EP | 2400506 | 12/2011 | |
| JP | 10-076018 A2 | 3/1998 | |
| JP | 10076018 | * 3/1998 | ............... A61N 5/10 |
| JP | 2009533086 | 9/2009 | |
| JP | 2010075338 | 4/2010 | |
| JP | 2011217880 | 11/2011 | |
| WO | 2011160915 | 12/2011 | |

OTHER PUBLICATIONS

PCT Written Opinion, Int Serial No. PCT/EP2013/054361, Int Filing Date: Mar. 5, 2013, Applicant: GSI Helmholtzzentrum Fur Schwerionenforschung GmbH, Date Mailed: Apr. 19, 2013.

German Office Action, Serial No. 10 2012 004 170.5, Applicant: GSI Helmholtzzentrum Fur Schwerionenforschung GmbH, Date Mailed: Dec. 13, 2012.

English Translation of Japanese Patent: JP 10-076018A2.

Schulte R. et al., "Design of a Proton Computed Tomography System for Applications in Proton Radiation Therapy", 2003 IEEE Nuclear Science Symposium Conference Record / 2003 IEEE Nuclear Science Symposium and Medical Imaging Conference, Portland, OR, Oct. 19-25, 2003.

"Sistema Aqua "Advanced Quality Assurance" Per IL Centro Nazionale Di Adoroterapia Oncologica", Feb. 15, 2008, Seiten 1-134, XP055005634, Gefunden im Internet; URL:http://project-aqua.web.cern.ch/project-aqua/RESOURCES/CNAO_TERA_REPORT.pdf.

Japanese Office Action, JP Patent Application No. 2014-560330, Applicant: Yuzuru Okabe, et al., Office Action Date: Nov. 27, 2015.

* cited by examiner

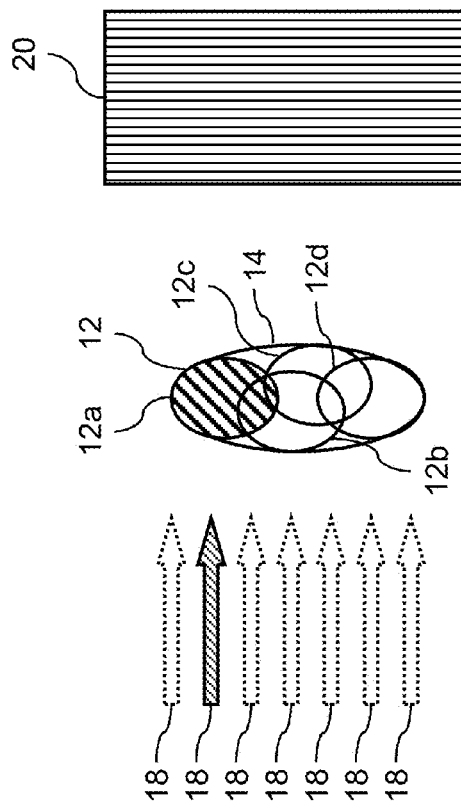
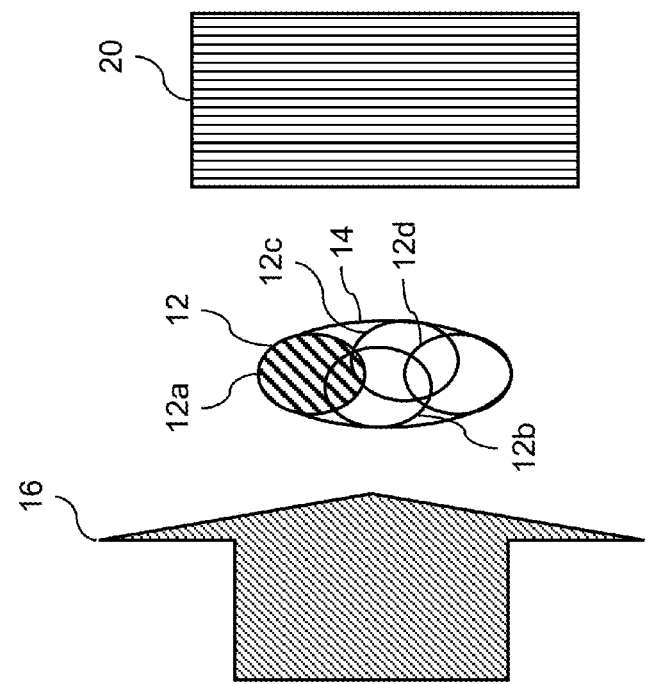

METHOD AND IRRADIATION INSTALLATION FOR IRRADIATING A TARGET VOLUME

TECHNICAL FIELD

The present disclosure relates to a method and an irradiation system for irradiating a target volume with an ion beam, for example for tumor therapy.

BACKGROUND

In ion beam therapy, a movement of the tumor is particularly challenging for the irradiation to ensure that the clinical target volume is covered with the prescribed dose despite the movement. For this purpose, specifically designed safety margins are typically used in ion beam therapy with a scattered beam, which has hitherto been considered sufficient.

With a scanned beam, however, interference effects will occur that require further measures. These include beam application using so-called gating, or so-called beam tracking, each of which are based on a movement detection system which supplies the tumor movement or a surrogate of the tumor movement, which is used in real time in order to optionally interrupt the beam (gating) or to cause active tracking (beam tracking). The quality of this signal has an influential role since the precision thereof has a direct impact on the precision of the total irradiation. Gating and beam tracking are generally known to those skilled in the art; for gating see e.g. "Respiratory Gated Irradiation System for Heavy-Ion Radiotherapy" by Shinichi Minohara et al. in Int. J. Oncology Biol. Phys., Vol. 47, No. 4, pp. 1097-1103, 2000, or "Gated Irradiation with Scanned Particle Beams" by Christoph Bert et al. in Int. J. Oncology Biol. Phys., Vol. 73, No. 4, pp. 1270-1275, 2009; and for beam tracking e.g. DE 10 2004 028 035 A1, each of which are hereby incorporated by reference.

Various movement detection systems are available on the market. Some movement detection systems measure a so-called movement surrogate, such as the breath temperature, the movement of the abdomen (in 1D, 2D, or 3D), the circumference of the abdomen/thorax, or the flow of breathing air. By contrast, other movement detection systems directly detect the movement of the tumor, for example based on fluoroscopy (with/without implanted radio-opaque markers), radio transponders, or ultrasound. In addition, combinations of these systems are used to combine their advantages, for example sparse fluoroscopy (high quality, but exposure dose for the patient) neuronally linked with an abdominal wall detection system (lower quality, but no exposure dose for the patient).

Movement detection systems for directly detecting the tumor movement often involve surgery in the patient or a significantly higher dose for the patient, for example in conventional X-ray fluoroscopy, especially when using high image acquisition rates. External surrogate-based movement detection systems are inherently limited to perform a very indirect measurement, which is why, among other things, the precision of the detection of the tumor movement needs to be improved. Furthermore, tumor movement may be highly complex, e.g. in case of a lung tumor, and may comprise translational, rotational, and compressive/dilatory components in all dimensions.

Moreover, all of the above systems consider the purely geometrical movement of the target volume, which in ion therapy is exclusively used in conjunction with, e.g., 4D CT datasets, since the range of the beam is influential. In fact, it is not only the spatial movement which is relevant for the precise deposition of the desired dose during irradiation, but rather the effect of the spatial movement on the energy loss of the ion beam, which may depend on other factors, such as the local distribution of tissue density.

Therefore, further improvements to these known methods are desirable, in particular with regard to the precision.

From EP 2 400 506 a device is known which generates at least two different particle beams, the second particle beam thereof being used to detect the movement of the target volume. For this purpose, two ion sources are used to produce ions of different types, which are brought together in a mixing chamber.

However, this method can only be used for certain combinations of ions and depends on the nature of the accelerator device. In addition, certain parameters of the two ion beams can only be influenced jointly. Therefore, the inventors searched for another solution, particularly in terms of complexity, flexibility, and the restrictions imposed by the entanglement of the two ion beams in the approach described in EP 2 400 506.

General Description

The present disclosure is therefore based on the object to provide a method and an irradiation system for irradiating a target volume with an ion beam, which allow high precision irradiation in spite of a moving target volume.

Another aspect of the object of the present disclosure is to provide a method and an irradiation system for irradiating a moving target volume with an ion beam, which enable to determine as accurately as possible the adverse effect of the movement of the target volume on the energy loss and the range of the ion beam in the target volume.

Yet another aspect of the object of the present disclosure is to provide a method and an irradiation system for irradiating a moving target volume with an ion beam, which allow for precise yet flexible movement detection of the target volume and which are independent of the accelerator device and can optionally even be easily retrofitted.

The object of the present disclosure is achieved by the subject matter of the independent claims. Various embodiments of the present disclosure are specified in the dependent claims.

A method is provided for irradiating a target volume that is moving during the irradiation with an ion beam. First, the ion beam is generated by an accelerator device and is accelerated and guided to the target volume. The accelerator device in particular comprises a circular accelerator such as a cyclotron or synchrotron, a linear accelerator, or a combination thereof.

The term ion beam in particular refers to a proton beam or a beam of heavier ions such as, e.g., oxygen or carbon. Such irradiation systems developed by the two applicants are found, e.g., at the GSI Helmholtz Centre for Heavy Ion Research in Darmstadt, and at the Heidelberg Ion Beam Therapy Center (HIT), where in particular $^{12}C$ ions are used for irradiation. However, other charged hadronic particle beams, such as pions etc., are not excluded.

According to the present disclosure, the irradiation of the target volume is divided over time into at least one radiography phase and at least one deposition phase, to alter the energy of the ion beam, i.e. one and the same ion beam, as a function of time between the at least one radiography phase and the at least one deposition phase, in a manner so that i) in the at least one radiography phase, the range of the ion beam is distal with respect to the target volume (behind the target volume as seen in beam direction), so that in the at least one radiography phase the ion beam passes through or screens the target volume to acquire an ion radiograph of the target volume using the ion beam, by detecting the ion beam after it has passed through the target volume using an ion radiography detector arranged distal with respect to the target volume; and ii) in the at least one deposition phase, the range of the ion beam is within the target volume, so that the ion beam is stopped in the target volume to deposit a predetermined dose in the target volume, namely the dose planned in the irradiation plan.

Ion radiography allows to detect the movement of the target volume, however, radiography and deposition are accomplished using one and the same ion beam, but with a different energy and consecutively in time. Therefore, in the radiography phase the beam range is adjusted such that the Bragg peak is located distally of the patient, and, more precisely, within the ion radiography detector, to measure the position of the Bragg peak using the energy-resolving and spatially resolving ion radiography detector by stopping the ion beam in the ion radiography detector. For this purpose, therefore, the energy of the ion beam is adjusted to a higher radiography energy in the radiography phase and to a lower deposition energy during the deposition phase. Thus, the alternation between radiography phase and deposition phase comprises an alternation of the energy of the ion beam.

For example, a carbon ion beam is generated which substantially completely passes through the target volume with an energy E' of about 600 MeV/u and which is used with this energy E' for radiography, and which is used with a reduced energy E in a range of about 250 MeV/u for dose deposition according to the irradiation plan.

Thus, both the dose deposition and the radiography can be performed with the same ion beam, and it suffice to merely alter or "switch" the energy. In this case, the alteration or switching of the energy of the beam may be effected during irradiation, in particular in real time, for example during a so-called spill in case of a synchrotron-based accelerator device, or in an irradiation pause between spills. The alteration or switching between the deposition energy and the radiography energy must not be confused with the much smaller change in energy for irradiating different isoenergy layers for which the beam range is altered by only a few millimeters and which is optionally performed additionally. Therefore, due to the temporal separation, certain parameters of the deposition and the ion radiography can be adjusted independently, in particular the lateral coverage of the target volume during a scanning process.

Accordingly, the present disclosure enables high-precision movement tracking. Range changes caused by the movement of the target volume can be directly determined from the ion radiographs, without using an error-prone conversion from the x-ray attenuation to the change in particle range. In fact, the ion radiograph "sees" the movement of the target volume in the same manner as during deposition, since the energy loss of the same ion beam is determined. The only difference between deposition and radiography is the energy of the ion beam, which minimizes the differences in the effect of the movement (translatory, rotary, compression/dilatation). In other words, ion radiography measures the same physical effect of the movement of the target volume which also occurs during deposition—except for the difference in ion energy, whose influence may, however, be calculated very accurately. Moreover, a lower dose can be assumed as compared to conventional fluoroscopy.

Moreover, the method can be carried out without major modifications of the accelerator device. Particularly easily, for example, the accelerator device is set to the higher radiography energy, and is then reduced from the higher radiography energy to the lower deposition energy in the deposition phase or phases by decelerating the ion beam using a passive energy modulator. In this manner it is possible to easily vary the energy of the ion beam rapidly enough to alternately irradiate the tumor (deposition) and to perform radiography and to be able to intervene in the irradiation in real time in response to the movement of the target volume for controlling purposes. For example, for this purpose, a digital, e.g. rotating pie-shaped energy modulator proximal with respect to the target volume (in front of the target volume as seen in the beam direction) with one pie segment missing is irradiated in order to modulate the energy and hence the range of the beam between a position in the target volume and a position distal with respect to the patient. In the area of the missing pie segment, the energy of the ion beam remains unchanged (radiography phase), and in the remaining area the energy of the ion beam is reduced to the deposition energy due to deceleration in the material of the modulator. Again, this particularly digital modulator must not to be confused with the known wedge systems for actively adjusting the beam range according to the movement of the target volume in beam tracking, which is optionally provided additionally.

Alternatively, the energy may be altered using binary modulator panels, such as described e.g. in "The PSI Gantry 2: a second generation proton scanning gantry" by Eros Pedroni et al. in Z. Med. Phys. 14 (2004), pp. 25-34, or by varying the settings on the flat-top in case of synchrotron-based acceleration, such as described e.g. in "Update of an Accelerator Control System for the New Treatment Facility at HIMAC" by Y. Iwata et al. in Proceedings of EPAC08, Genoa, Italy, pp. 1800-1802, which are hereby incorporated by reference in this regard. However, it is also possible to use a so-called Cyc-LINAC, such as described e.g. in "High Frequency Linacs for Hadron Therapy" by Ugo Amaldi et al. in Reviews of Accelerator Science and Technology, Vol. 2 (2009), pp. 111-131, which is hereby incorporated by reference in this regard. In the Cyc-LINAC, jumps in range of an order of magnitude as required for the alternation between the radiography energy and deposition energy can be effected by turning off and on individual cavities of the linear accelerator. Thus, the variation in energy may be only effected following the acceleration in the accelerator device (passive modulator), or at the end of acceleration (Cyc-LINAC), at least preferably not before the acceleration.

Accordingly, the ion radiography detector is in particular an energy-resolving detector which measures the (remaining) energy of the ion beam after it has passed through the target volume. Based thereon, the energy loss caused by the passage through the target volume can be calculated, and from this, in turn, the effect of the movement of the target volume on the deposition can be determined.

Thus, one and the same ion beam is in particular used for the deposition and for the ion radiography, in the sense that the ion species and the charge are identical and only the energy is different. That is, one and the same ion beam is used, whose energy is varied consecutively in time, rather than two different ion beams at the same time.

In other words, with the above condition, ion radiography and deposition are performed consecutively in time and independently of one another. In particular, there will be no deposition during the radiography phase and/or no ion radiography during the deposition phase.

According to a preferred embodiment of the present disclosure, the irradiation of the target volume is divided over time into a plurality of radiography phases and a plurality of deposition phases, wherein between the radiography phases and the deposition phases the energy of the ion beam is alternately switched up and down, so that in alternating cycles:
i) in the radiography phases, the range of the ion beam is distal with respect to the target volume, so that in the radiography phases the ion beam passes through or screens the target volume and ion radiographs of the target volume are acquired by means of the ion beam by detecting the ion beam using an ion radiography detector that is arranged distal with respect to the target volume; and
ii) in the deposition phases, the range of the ion beam is within the target volume, so that the ion beam is stopped in the target volume to deposit a respective predetermined dose in the target volume.

Furthermore, the timing of the radiography phases may be matched with the movement phases of the target volume. Alternatively or additionally, the timing of the radiography phases may be matched with the extraction phases of the accelerator device (e.g. spills in a synchrotron) and/or with the timing of the irradiation of the isoenergy layers, if the target volume is divided into isoenergy layers that are irradiated successively.

If in the deposition phases different isoenergy layers of the target volume are targeted with the ion beam in order to deposit a respective predetermined dose in the isoenergy layers, for example, a radiography measurement according to i) may be performed at least prior to the irradiation for depositing a dose in each isoenergy layer, and/or an ion radiography measurement is performed at the beginning of each movement phase or each spill.

The intensity of the ion beam may be set to be considerably higher in the at least one or the plurality of deposition phases than in the at least one or the plurality of radiography phases, which may also be controlled in real time. This permits to keep the dose to the patient low.

If the target volume is cyclically moving during irradiation, such as, e.g., a lung tumor while breathing, the cyclic movement of the target volume is divided into a plurality of movement phases. In conjunction with the present disclosure it is helpful if the duration of the at least one radiography phase or the plurality of radiography phases is chosen so as to be not greater than the duration of each of the movement phases. In this case, if desired, a ion radiography measurement may be performed in each movement phase, preferably at the beginning thereof. In other words, steps i) and ii) as defined above are performed in the same movement phase, i.e. the radiography phase and the deposition phase are at least partly in the same movement phase.

Accordingly, this permits to achieve a particularly precise and reliable movement tracking.

The present disclosure is combined with an irradiation with active ion beam tracking to compensate for the movement of the target volume (so-called beam tracking). The active tracking movement of the ion beam, i.e. beam tracking, may be controlled based on the ion radiography measurement performed by the ion radiography detector. This controlling of the active tracking movement of the ion beam (beam tracking) in response to the radiography measurement may as well be performed in real time.

Moreover, due to the temporal separation of the radiography and the deposition, the ion beam can be controlled independently in the radiography phase and in the deposition phase. In particular, in the radiography phase the ion beam can be driven across the lateral extent of the target volume, independently of the deposition.

According to a preferred embodiment of the present disclosure, the ion radiography detector is designed as a spatially resolving detector, so that in the at least one or the plurality of radiography phases a laterally two-dimensionally spatially resolved ion radiograph is acquired, preferably at least of portions of the Internal Target Volume (ITV, according to ICRU 62), by passing through a plurality of grid points of the target volume and determining the range of the ion beam after it has passed through the target volume for each of the grid points in the ion radiograph to create an at least two-dimensional map of the (water equivalent) range of the ion beam. This map of the range of the ion beam can be used, for example, as a monitoring or control information for at least one subsequent deposition phase.

An at least two-dimensional representation of the target volume in the ion radiograph allows a particularly precise and reliable tracking of the movement of the target volume.

When the irradiation method is a scanning method, for example a raster scanning method, the ion beam in form of a so-called pencil beam is scanned across at least a portion of the clinical target volume in the at least one deposition phase or the plurality of deposition phases, and is wobbled across at least a portion of the lateral area of the target volume in the at least one radiography phase or the plurality of radiography phases.

Accordingly, despite of using a fine pencil beam, a lateral two-dimensional ion radiograph can be acquired in this manner. The wobbling for radiography measurement can be performed independently of the scanning during deposition.

Moreover, this allows for a finer pre-calculation of range losses than on a grid point basis, if desired. For the wobbling, for example, during which the beam is moved quickly over a rather large area, more or even all positions can be compared directly, without being limited to nominal grid positions. A finer resolution may, for example, be of the order of the CT voxel size. CT voxel size is, e.g., only about 1 mm, while the spacing of the grid points during the irradiation with the scanning method typically ranges from 2 to 3 mm.

During the scanning process, in the at least one or the plurality of deposition phases, the ion beam is scanned across the Clinical Target Volume (CTV, according to ICRU 50). In the at least one or the plurality of radiography phases, the ion beam may be wobbled across at least a portion of the lateral area of the Internal Target Volume (ITV, according to ICRU 62) beyond the clinical target volume.

By such rapid wobbling, the lateral position of the beam is driven across all areas of the internal target volume (ITV) and thus across the integral extent of the clinical target volume in all its phases of movement. This wobbling across the entire internal target volume may be performed in a time interval between 1 ms and 1000 ms, for example in a range of about 10 ms, 50 ms, 100 ms, or 500 ms, so that a lateral two-dimensional radiograph of the internal target volume can be acquired during this time interval.

In other words, if an area larger than the clinical target volume (CTV) is irradiated in the radiography measurement, especially if at least the internal target volume (ITV) is covered which represents the clinical target volume (CTV) in all states of movement, the entire range of movement of the target volume can be covered.

Furthermore, a range simulation calculation may be performed in order to calculate simulated target values for the range of the ion beam. In this case, during the irradiation in the radiography phase, the actual (water equivalent) range of the ion beam after having passed through the target volume is determined, and the determined actual ranges are compared with the simulated target values.

Moreover, the range simulation calculation is performed for a plurality of grid points and a multi-dimensional map of simulated target values (so-called "range map") of the range of the ion beam is created. In this case, during the irradiation in the radiography phase, the actual range of the ion beam after having passed through the target volume is determined, again for a plurality of grid points, and based thereon a multi-dimensional ion radiograph with the respective actual ranges of the ion beam is produced, and the ion radiograph is compared with the map of simulated target values.

By precalculating a map of simulated ranges, in particular a so-called digitally reconstructed range map (DRRM), and by respectively comparing the measurement and the simulation calculation, it is possible to match the movement of the target volume with the movement of the ion beam, which, optionally, allows not only to acquire parameters related to the movement and range change, but also to the interference between the two latter, especially the interplay or pattern.

According to a further preferred embodiment of the present disclosure, the movement of the target volume or a movement surrogate is measured using an appropriate internal or external movement measuring system (sometimes referred to as a motion sensor). According to the present disclosure, the measurement results are automatically associated with the ion radiographs acquired by the ion radiography detector, e.g. by an appropriately programmed microcomputer, and the irradiation is controlled based on the associated data.

However, it is also easily possible to control the alternation between the radiography phases and the deposition phases in response to the measurement results of the movement measuring system.

For example, in a combination with the external movement surrogate, the surrogate information is used to determine a movement phase in which it is verified using a radiograph if the clinical target volume (CTV) or individual monitored points of the clinical target volume (CTV) are in the location as planned.

Furthermore, in the at least one or the plurality of radiography phases the target volume may be irradiated from more than one direction, and in this manner a more than two-dimensional ion radiograph ("2.5D detection") is acquired, at least locally. This is helpful for irradiation sites where more than one beam tube is available. In this case it is possible to acquire radiographs from more than one direction and thus to enable 2.5D detection. Furthermore, an irradiation similar to "RapicArc" is conceivable with a gantry, so that in this case, again, radiographs can be acquired from different directions within the duration of irradiation, and thus a 3D movement plus range can be reconstructed using suitable reconstruction algorithms. This even enables acquisition of a 4D ion CT.

In total, this provides very comprehensive information about the movement of the target volume.

In summary, the collected data should be evaluated with respect to the expectation in real time, for which purpose the methods known from fluoroscopy can be used, i.e., inter alia, a comparison between measurement and digitally reconstructed range map (DRRM) (even in 4D, i.e. one DRRM per movement phase of the 4D CT), or correlation models between radiography and other surrogates or simultaneously acquired fluoroscopy/radiography data are used.

According to a simple aspect of the present disclosure, in response to the acquired ion radiograph, if predetermined threshold values are exceeded, for example when comparing range simulation and energy loss measurement, an interlock signal is generated, by means of which the irradiation is interrupted.

Thus, the present disclosure is in principle not restricted to movement monitoring alone, rather a verification of the acquired DRRMs is possible, so that for example in case of excessive deviations the irradiation can be interrupted and may optionally even be re-planned. In this case the ion radiography detector measures the ion energy, and thus the particle range which is a relevant factor for the dose is directly detected (in contrast to methods which only detect equivalent values).

Depending on the contrast in the irradiated anatomical region, it is also possible to implant markers (gold spheres, carbon spheres, etc.) to define visible points in the ion radiograph. The present disclosure is furthermore also applicable to irradiation with inter-fractionary movement or to static head-and-neck irradiation, for example to enable positioning or to provide an interlock signal in the event that nevertheless unexpected movements do occur.

The present disclosure also provides an irradiation system for irradiating a moving target volume with an ion beam, which permits to perform the method described above. For this purpose, the irradiation system comprises:

an accelerator and beam guiding device for generating and accelerating an ion beam and for guiding and directing the ion beam onto the target volume;

a controller device for controlling the irradiation system;

a device for varying the energy of the ion beam over time during the irradiation or in an irradiation pause, between at least one radiography phase and at least one deposition phase, especially in addition to the alteration in range for dose deposition in different isoenergy layers, which device is adapted i) in the at least one radiography phase, to adjust the energy of the ion beam to a higher radiography energy, with a range distal with respect to the target volume or distal to the patient (behind, as seen in the beam direction), more precisely within the ion radiography detector, so that the ion beam passes through or screens the target volume;

ii) in the at least one deposition phase, to adjust the energy of the ion beam to a lower deposition energy, with a range in the target volume and so that the ion beam is stopped in the target volume to deposit the planned dose in the target volume; and an ion radiography detector arranged distal with respect to the target volume for acquiring ion radiographs of the target volume by stopping and detecting the ion beam that has passed through the target volume in the ion radiography detector during the radiography phase.

The means for varying the energy of the ion beam over time may alternately switch up and down the energy of the ion beam between the radiography energy and the deposition energy in a cyclic sequence that includes a plurality of radiography phases and a plurality of deposition phases, in particular during the irradiation or in an irradiation pause, and in addition to the alteration of range for targeting the isoenergy layers in the deposition phase.

The ion radiography detector in particular has a temporal resolution sufficient to produce a new radiograph in each radiography phase, in order to be capable to optionally control the irradiation in real time.

The controller device may control the irradiation system in a manner so that in the deposition phases different isoenergy layers of the target volume are targeted with the ion beam to deposit a respective predetermined dose in each of the isoenergy layers, and so that at least before the irradiation for dose deposition in each isoenergy layer a radiography measurement is performed using the ion radiography detector.

A passive energy modulator may be used, and in this case the ion beam is first generated by the accelerator device with the radiography energy, and in the deposition phase the energy of the ion beam is reduced to the deposition energy by deceleration in the material of the energy modulator. The passive energy modulator may, for example, be a round plate having a pie-segment-shaped cutout and is rotating in the ion beam, so that in cyclically alternating periods the ion beam passes through the material of the plate and is thereby decelerated to the deposition energy (deposition phase) or passes unattenuated through the pie-segment-shaped cutout (radiography phase).

Furthermore, the controller device may control the irradiation system such that during deposition in the target volume the intensity of the ion beam is higher than during the radiography measurement, to keep the additional radiation exposure caused by the radiography measurement low for the patient.

In preparation of the irradiation, a microcomputer may divide the movement of a cyclically moving target volume, e.g. due to breathing, into several movement phases. When a pie-shaped energy modulator is used, the shape and rotational speed thereof may be adapted to the duration of the movement phases in a manner so that the duration of the radiography phases is shorter than the duration of the movement phases.

If means for active ion beam tracking are provided to compensate for the movement of the target volume (beam tracking), the controller device may be operatively connected therewith for controlling the beam tracking process in response to the ion radiographs acquired using the ion radiography detector.

The ion radiography detector may include an energy resolving and spatially resolving detector which acquires an energy resolved and laterally two-dimensionally spatially resolved ion radiograph in each case, at least of portions of the internal target volume (ITV). A computing means then determines the range of the ion beam after it has passed through the target volume for each of the grid points and creates a two-dimensional map of the range of the ion beam after having passed through the target volume.

The scanning device that may be provided for scanning the ion pencil beam (diameter of typically a few millimeters) is controlled by the controller device in a manner so that for dose deposition the ion beam is scanned across the target volume in two or three dimensions, and so that for radiography the ion beam is wobbled across at least a portion of the lateral area of the target volume, independently of the scanning for deposition purposes because consecutively in time. The same scanning magnets may be used for the scanning and the wobbling, but it is as well possible to install separate magnets for the wobbling process, for example in case the scanning magnets are not fast enough for wobbling.

For example, the controller device controls the scanning device (with or without separate wobbling magnets) so that during dose deposition the ion beam is scanned across the clinical target volume (CTV, ICRU 50), and during radiographing it is wobbled across a greater lateral area than the clinical target volume, in particular across the internal target volume (ITV, ICRU 62).

The range simulation calculation described above is typically performed by a suitably programmed microcomputer which also performs the comparison with the determined actual ranges and then generates control signals, preferably in real time, which are used, for example, to adapt or interrupt the irradiation. The same applies to the embodiment in which the actually measured multi-dimensional radiographs are compared with the map of simulated target values.

In particular, the controller device receives the measurement results of the movement measuring system and the ion radiographs of the ion radiography detector to automatically associate the measurement results and the ion radiographs, and then controls the irradiation in response to these associated data.

Alternatively, the controller device controls the alternation between the radiography phases and the deposition phases in response to the measurement results of the movement measuring system.

Moreover, the irradiation system may include a plurality of beam tubes and/or a rotatable gantry, by means of which the target volume can be irradiated from more than one direction to acquire a locally more than two-dimensional ion radiograph.

The method and the irradiation system of the present disclosure are in particular adapted for tumor therapy. However, they may also be used to irradiate a target volume which does not belong to a human or animal body. For example, a phantom which, by way of example, includes a target volume for movement simulation, may be irradiated.

The present disclosure will now be described in more detail by way of exemplary embodiments and with reference to the figures, in which identical and similar elements are partly designated with the same reference numerals, and wherein the features of the various exemplary embodiments can be combined.

BRIEF DESCRIPTION OF THE FIGURES

In the drawings:

FIG. 1 is a schematic diagram illustrating the irradiation of a moving target volume using a scattered ion beam;

FIG. 2 is a schematic diagram illustrating the irradiation of a moving target volume using a scanning ion beam;

DETAILED DESCRIPTION

Figure 3:
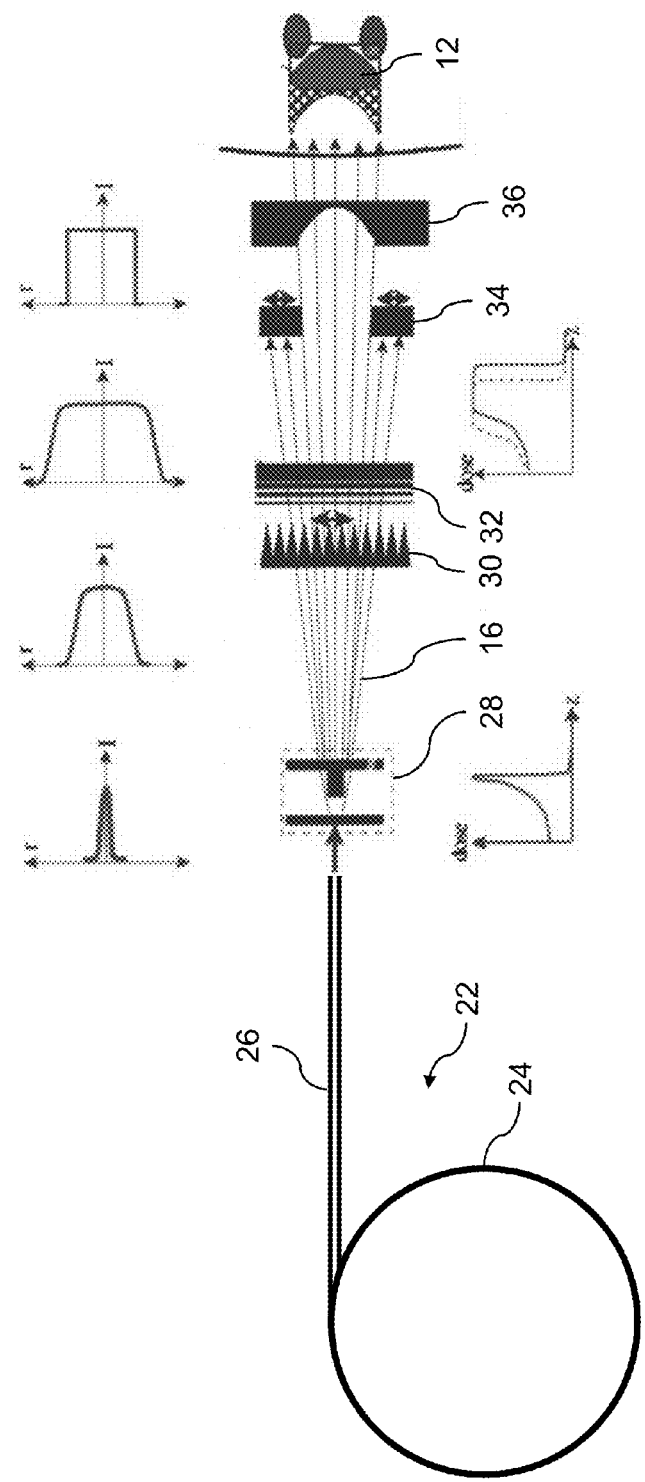
FIG. 3 is a schematic diagram of an irradiation system with a scattered ion beam according to the prior art.

FIG. 1 shows a tumor as a clinical target volume 12 (CTV) according to ICRU 50 in a reference phase of movement 12a. The tumor 12 moves within an envelope which represents movement conditions 12a, 12b, 12c, and 12d, for example. The envelope defines the internal target volume 14 (ITV) according to ICRU 62.

In a passive irradiation with scattered ion beam 16, further measures for acquiring information about the range distribution in the entire internal target volume 14 by means of the ion radiography detector 20 using the radiography measurement are usually not required because, anyway, the entire internal target volume 14 is irradiated simultaneously.

FIG. 2 illustrates the irradiation of the clinical target volume 12 with a scanning ion beam 18. Here, in order to acquire information on the range distribution in the entire internal target volume 14 by means of the radiography measurement using the ion radiography detector 20, the ion beam is wobbled across the entire internal target volume 14, which is schematically symbolized by dotted arrows 18. During wobbling, the fine pencil beam is rapidly moved across the lateral extent of the entire internal target volume 14, only one dimension thereof being shown in FIG. 2 since the second lateral dimension is perpendicular to the plane of the drawing.

Optionally, the measured range distribution is compared, for example with a digitally reconstructed range map (DRRM). Alternatively, however, information about the current beam position or several different beam positions may as well be obtained by comparing the radiography measurement performed using the ion radiography detector 20 at the current grid position or at several representatively targeted grid positions with a DRRM.

In other words, the digitally reconstructed range maps (DRRM) include the expected range loss of the radiography beam which is radiated from its defined direction at a defined position with a defined energy through a CT (or a phase of a 4D CT), for a plurality of beams. During radiography, the measured values of the radiography measurement are compared with the DRRM. In this manner, for example, the determination of movement phases of a movement surrogate is verified, or the movement phase is determined independently in response to the radiography measurement.

FIG. 3 shows a known irradiation system 1 with an accelerator device 22 comprising a cyclotron 24 and beam guiding means 26. The ion beam 16 is scattered using a scattering system 28. Then, the range is enlarged using a range modulator 30 and a range shifter 32. Subsequently, the scattered ion beam 16 is collimated to the extent of the internal target volume using a collimator 34. The dose field is adapted to the distal contour of the target volume using a compensator 36. The originally fine ion beam 16 as emitted from the accelerator device 22 is adapted to the target volume using the scattering system and several subsequent passive beamformers. This represents a completely passive beam modeling system.

Figure 4:
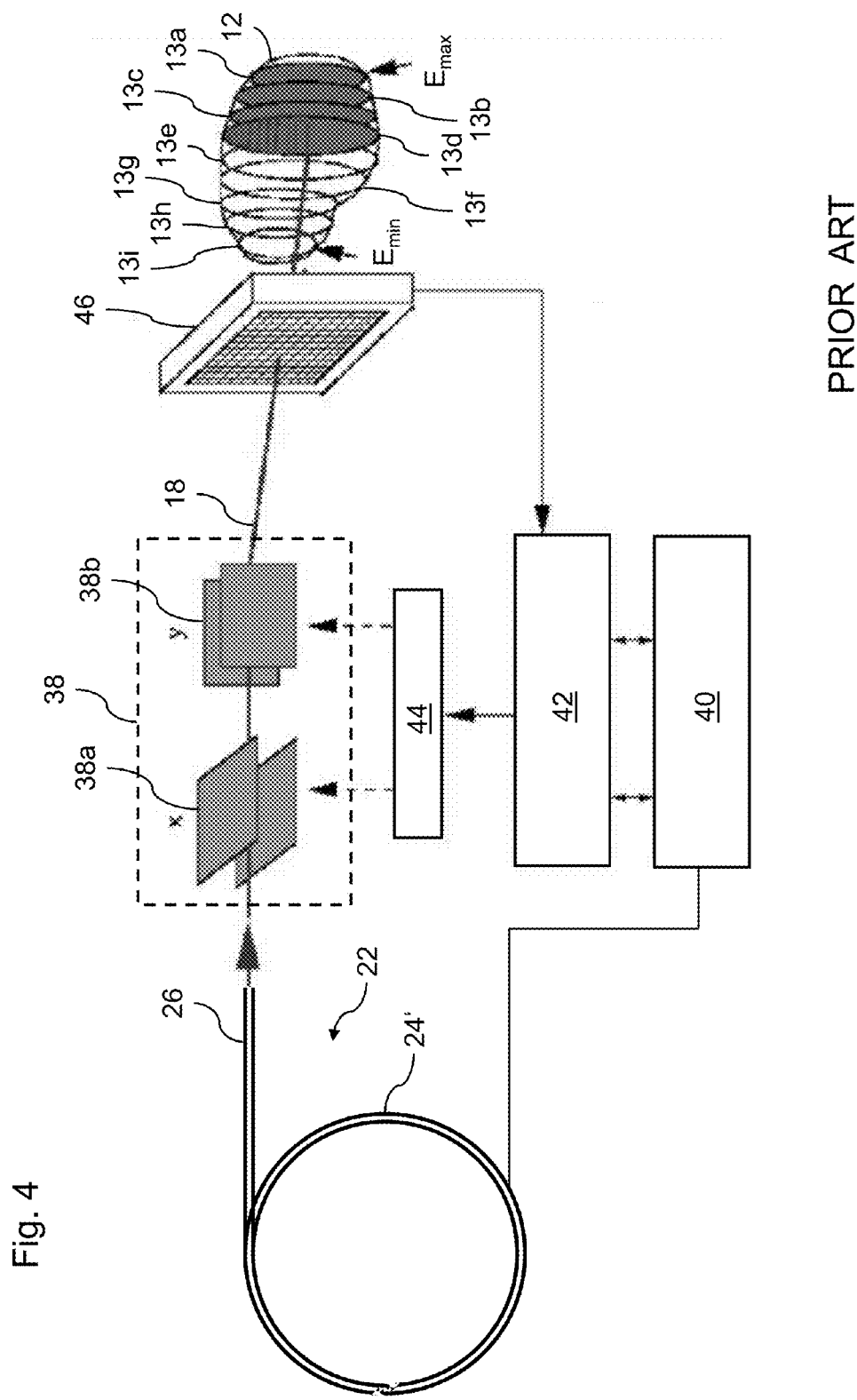
FIG. 4 is a schematic diagram of an irradiation system with a scanning ion beam according to the prior art.

FIG. 4 shows a known irradiation system 1 with an intensity-controlled magnetic scanning system, such as for example used at GSI in Darmstadt. In this example, the accelerator device 22 comprises a synchrotron 24' and beam guiding means 26 which guide the ion beam into the irradiation room (not shown) to irradiate the target volume 12 there. The fine ion beam 18, referred to as a pencil beam, is scanned across the lateral extent of the target volume using a scanning device 38 that comprises fast scanning magnets 38a, 38b for scanning the ion beam 18 in the X and Y directions. In order to scan the target volume in three dimensions, the Bragg peak is scanned across a plurality of isoenergy layers 13a to 13i. The ion beam 18 is, for example, a $^{12}$C ion beam with 80 to 430 MeV/u. The appropriate beam parameters of the ion beam 18 are controlled by the synchrotron control system 40 and provided by synchrotron 24' in form of pulses. Typically, these isoenergy layers 13a to 13i are scanned from distal (highest energy $E_{max}$) to proximal (lowest energy, $E_{min}$). The scanning of the target volume 12 is initially prepared in a preparatory phase, the so-called irradiation planning in which an irradiation plan is calculated and defined which is stored in therapy control system 42. The therapy control system 42 is operatively interconnected with the synchrotron control system 40 to control, among other things, the power supply 44 of scanning device 38 to target the respective grid point for dose deposition. Furthermore, the beam position is monitored by a beam position monitor 46, and is transferred to the therapy control system 42.

Figure 5:
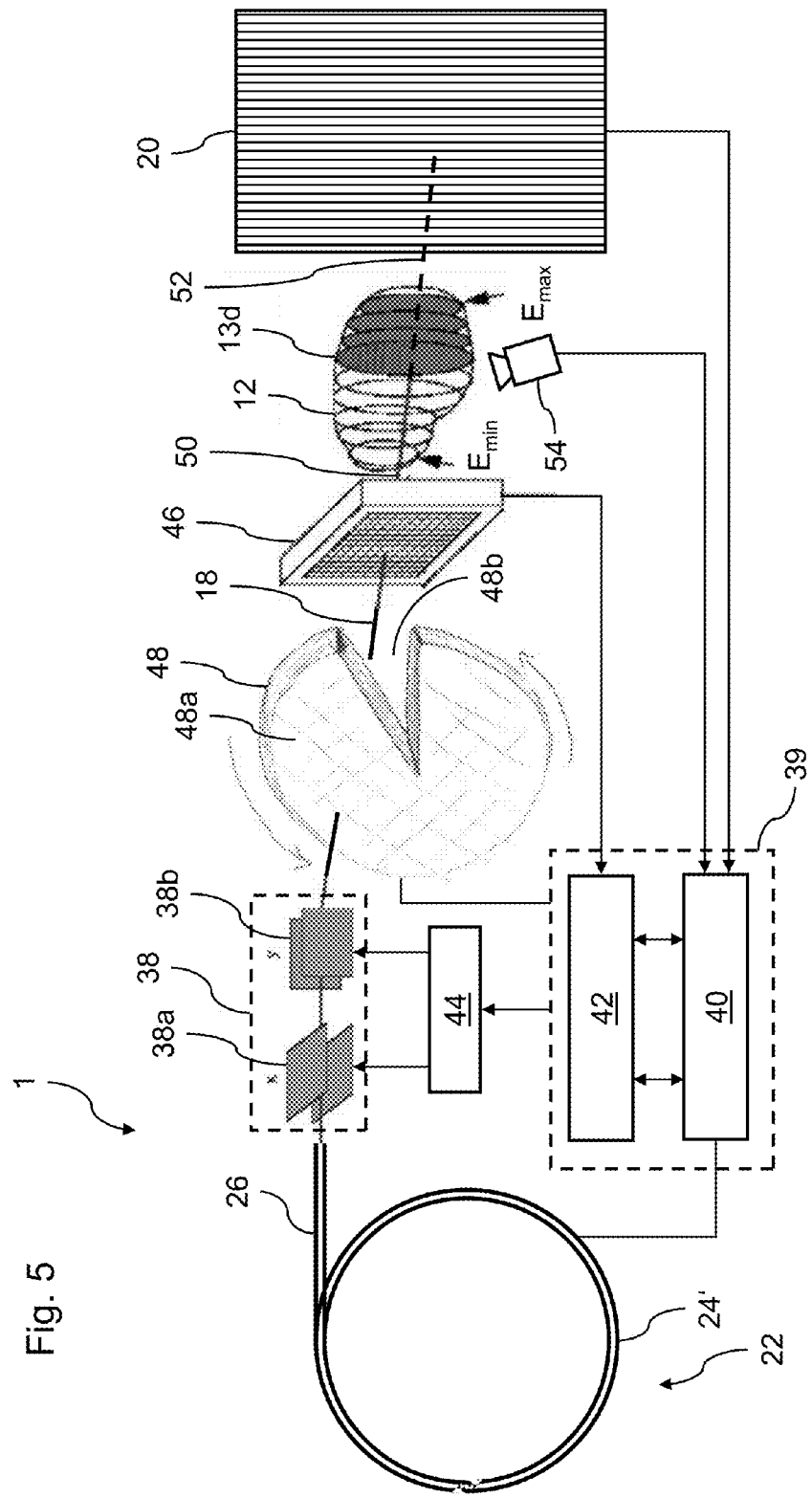
FIG. 5 is a schematic diagram of an irradiation system with a scanning ion beam and an energy modulator according to one embodiment of the present disclosure.

Referring to FIG. 5, an irradiation system with a scanning system 38 as in FIG. 4 is shown, but now according to the present disclosure a pie-shaped energy modulator 48 is located proximal with respect to the target volume, or proximal with respect to the beam position monitor 46. In this example, the energy modulator 48 is disposed distal with respect to the scanning device 38. The actual irradiation of the target volume 12, i.e. dose deposition, is performed with a therapy energy or deposition energy E. However, the accelerator device 22 provides the much higher radiography energy E'=E+dE, wherein dE corresponds to the energy loss when passing through the pie-shaped energy modulator 48. Energy modulator 48 is rotating to define the time sequence between deposition phases and radiography phases. In the time intervals in which the energy modulator is irradiated and the radiation passes through the solid portion 48a which comprises the modulation material, the energy modulator 48 modulates down the ion beam energy from the radiography energy E' to the deposition energy E, so that the target volume can be irradiated as usual, which is represented by the solid line 50. In the time interval in which the ion beam passes through the recess 48b of the energy modulator, there will be no energy loss dE, so that the radiography energy E'=E+dE arrives at the patient. The radiography energy E' or the energy loss dE is chosen to be sufficiently large so that the ion beam completely passes through the target volume and in case of therapeutic irradiation through the entire patient, which is represented by the dashed line 52. In this case, the spatially and energy resolving ion radiography detector 20 which is arranged distal with respect to the target volume 12 and has a size that should cover at least the entire internal target volume, can be used to measure the energy loss in the target volume 12 or in the patient, with spatial resolution. Accordingly, in this radiography phase an ion radiography measurement is performed at the radiography energy E' using the ion radiography detector 20. For example, the radiography energy is E'=600 MeV/u, the deposition energy is about E=250 MeV/u, and the energy loss in the energy modulator is about dE=350 MeV/u.

In this example, the spatially and energy resolving ion radiography detector 20 comprises a stack of up to 61 parallel ionization chambers, with PMMA absorber sheets arranged therebetween. The thickness of the absorber sheets is chosen between 0.5 mm and 5 mm, depending on the requirements. The ion radiography detector 20 may furthermore comprise a fixed or variable pre-absorber which reduces the water-equivalent range by 90 mm or by up to 90 mm. The active area of the ion radiography detector 20 is, for example, 300×300 mm$^2$ in order to provide at least a measuring field of 200×200 mm$^2$ for the ion beam 18.

The energy modulator 48 is operatively connected to the controller device 39 of the irradiation system 1. The controller device 39 may control the rotation of the energy modulator 48, and/or the energy modulator 48 provides feedback about its current angular position to the controller device 39, for timing and synchronizing the control of the accelerator device 22, the scanning device 38, and the radiography phases and deposition phases defined by the rotating energy modulator 48, inter alia.

Irradiation system 1 additionally comprises a movement measuring system 54 which is per se known and which transmits information about the movement of the target volume 12 to the controller device 39. This may be a direct movement information in case of an internal movement measuring system, or a surrogate information in case of an external movement measuring system.

For use as the additional internal or external movement measuring system 54, the following systems are considered, for example. As an internal movement measuring system:
  kV/MV imaging (photon) fluoroscopy
    with implanted markers
    without implanted markers
  implanted electromagnetic transponders
  ultrasonography
and as an external movement measurement system for measuring a movement surrogate:
  measurement of the patient's breath:
    volume measurement
    temperature measurement
    measurement of the air flow rate
  measurement on the patient's surface
    filming of applied markers (e.g. infrared emitters)
    stereo camera for filming the body surface
It is also possible to combine several movement measuring systems.

Figure 6:
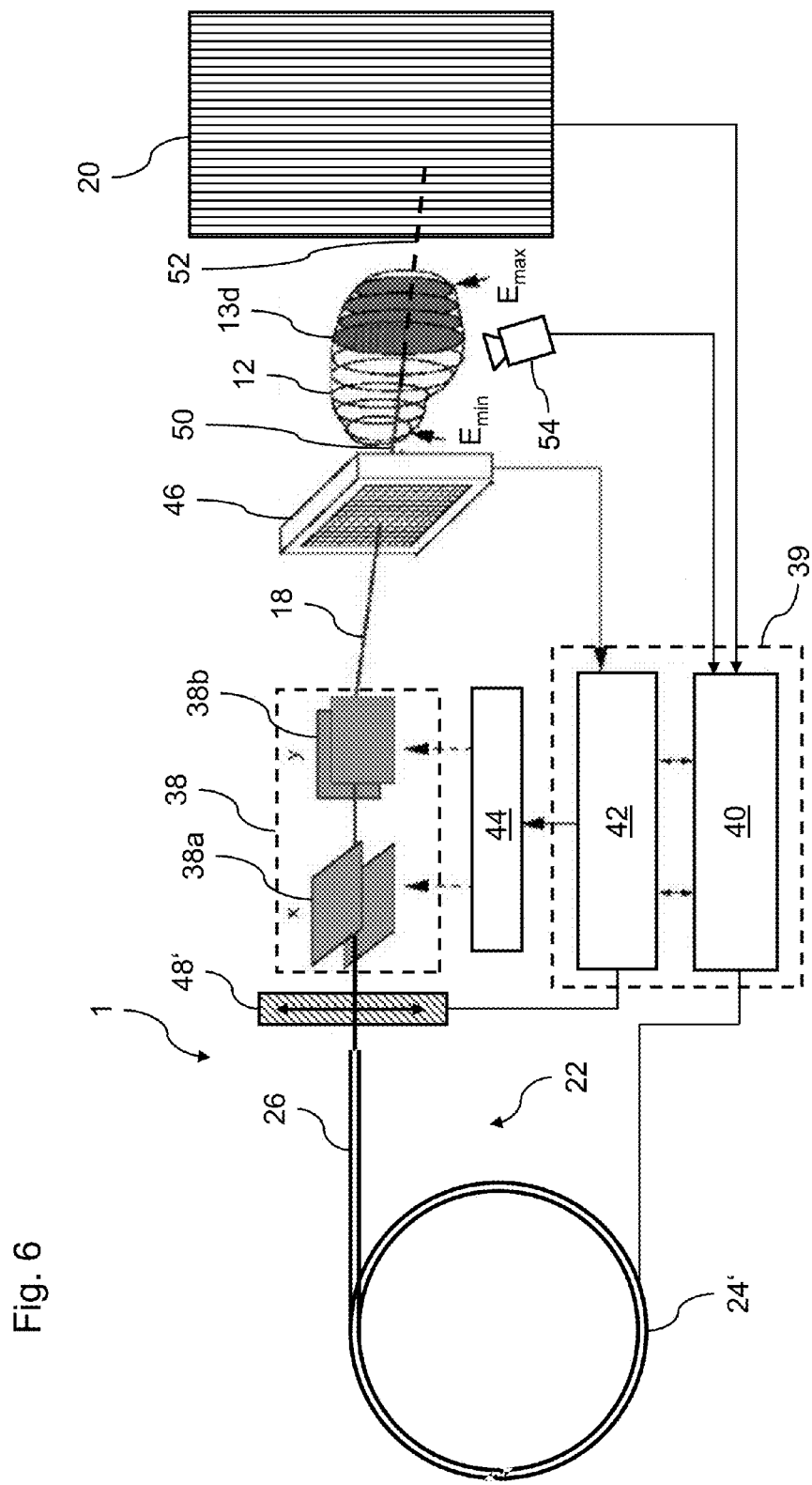
FIG. 6 is a schematic diagram of an irradiation system with a scanning ion beam and an energy modulator according to another embodiment of the present disclosure.

Referring to FIG. 6, an alternative embodiment of the present disclosure is illustrated in which the energy modulator is disposed proximal with respect to the scanning device 38. In the present example, the energy modulator is configured as a binary energy modulator plate 48' which defines the reduction of beam energy from the radiography energy to the deposition energy by introducing and retracting the energy modulator plate 48' into and out of the beam path of the ion beam 18. By retracting the energy modulator plate 48', the beam energy is increased from the deposition energy E to the radiography energy, E'=E+dE, so that the target volume 12 and in tumor therapy the entire patient is penetrated by the ion beam, in order to allow for the radiography measurement. By introducing the energy modulator plate 48', the radiography energy E' delivered by the accelerator device is reduced by dE to the deposition energy E in order to irradiate the target volume 12 in a manner so that the dose specified in the irradiation plan is deposited, which is represented by solid line 50 in FIG. 6 in which, by way of example, the fourth isoenergy layer 13d as seen from a distal perspective is irradiated.

Since in this example the energy modulator 48' is arranged proximal with respect to the scanning device 38, the scanning device 38 and possibly further magnets of the beamline arranged distal with respect to the energy modulator 48' have to be readjusted. This may be accomplished in real time with appropriately fast magnet systems and controlled by controller device 39. In having the energy modulator arranged upstream, the scanning device 38 is a lower exposure for the patient to fragments which are generated in the energy modulator. In having the energy modulator arranged distal with respect to the scanning device, or in front of the patient, as illustrated in FIG. 5, a corresponding readjustment of the scanning device 38 and of further beam guiding elements can be dispensed with.

Figure 7:
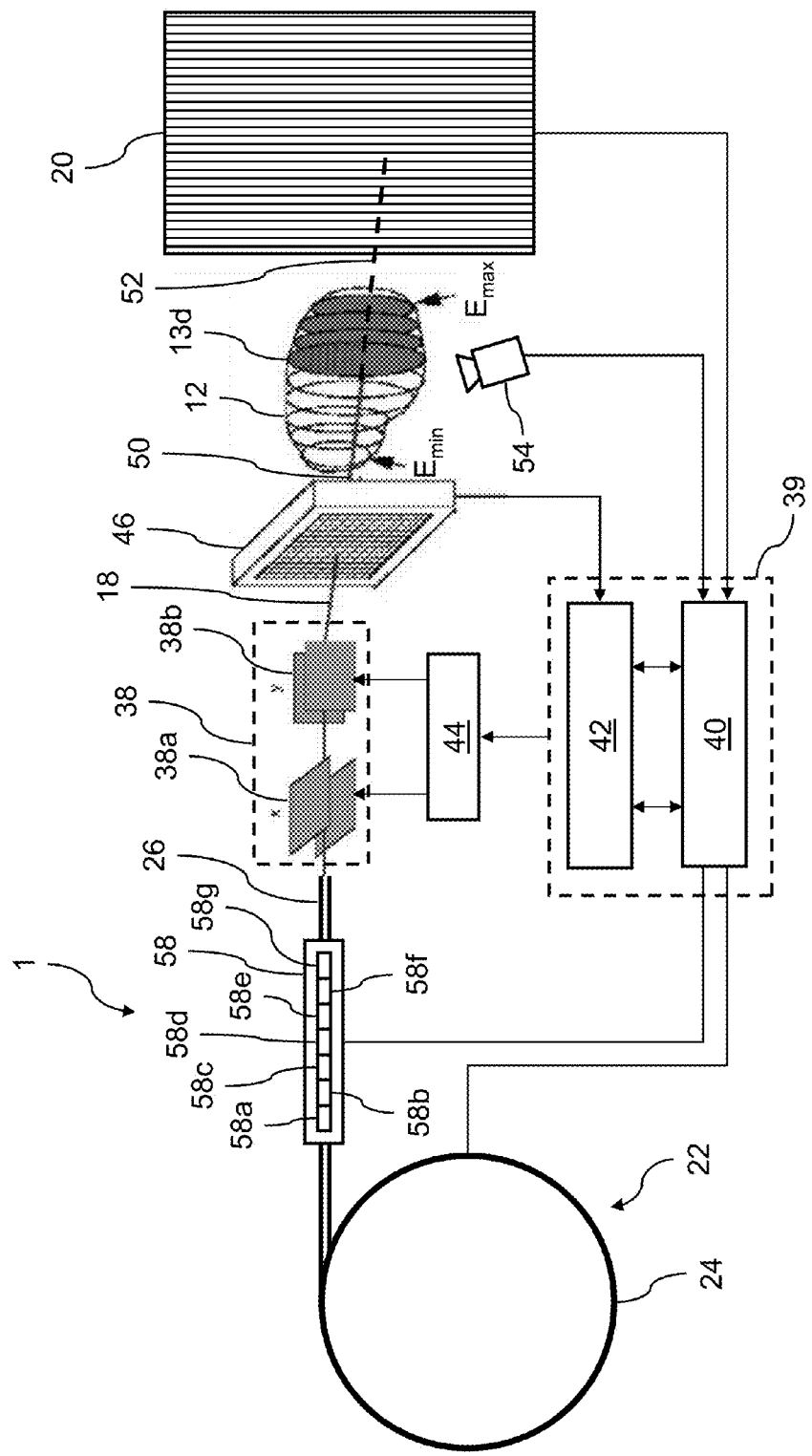
FIG. 7 is a schematic diagram illustrating an irradiation system with a downstream linear accelerator according to a further embodiment of the present disclosure.

FIG. 7 shows a further embodiment, in which the energy variation between the radiography energy and the deposition energy is effected by the accelerator device 22. Suitable for this purpose, for example, is a cyclotron 24 with a downstream linear accelerator 58. Otherwise, the configuration is substantially similar to that of FIGS. 5 and 6. In contrast to the passive energy modulators 48, 48' used in FIGS. 5 and 6, in this example the alteration in energy between the deposition energy and the radiography energy can be accomplished with the downstream linear accelerator 58. For the deposition phase, one or more of accelerator cavities 58a to 58g are turned off to reduce the energy of the ion beam from the radiography energy to the deposition energy. For this purpose, the Cyc-LINAC described in the Review paper by Ugo Amaldi et al. cited above may be used, for example.

Figure 8:
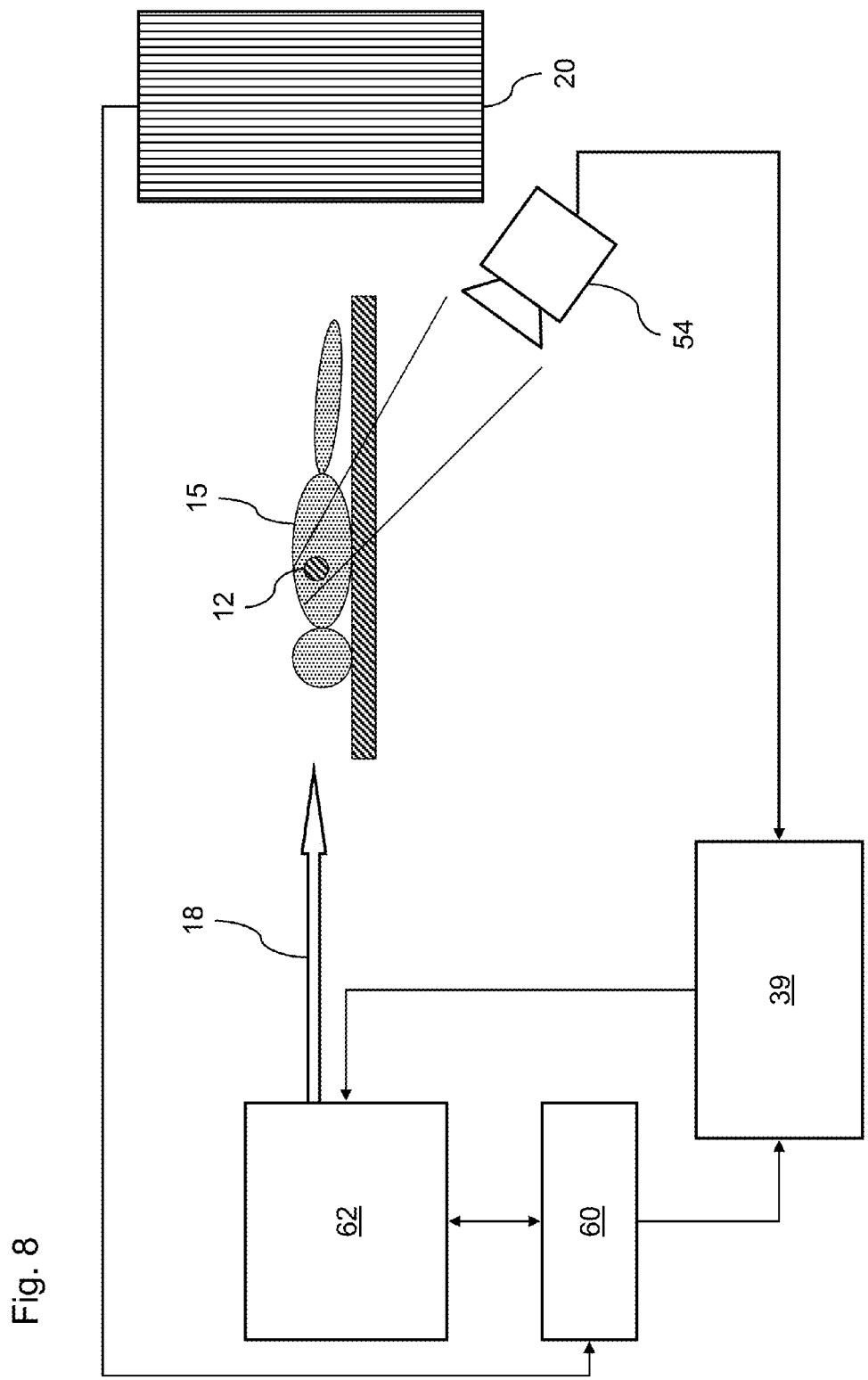
FIG. 8 is a schematic diagram illustrating the irradiation of a target volume in combination with a movement measuring system.

FIG. 8 shows the combination of movement measuring system 54 with the radiography measurement by means of radiography detector 20 according to the present disclosure. The per se known movement measuring system 54 transfers the data about the movement of the target volume to controller device 39. In the radiography phase, ion radiography detector 20 acquires ion radiographs of the target volume (and the surrounding tissue) by means of the ion beam 18 that passes through the target volume 12 or the patient 15, respectively. Controller device 39 compares the ion radiography measurements 60 with the measurements of the movement measuring system 54 which, for example, may comprise a surrogate in form of a stereo camera image of the patient's thorax. First, the movement measuring system 54 can be used to determine the movement phase of the patient in a per se known manner. When controller device 39 determines that the movement phase determined using the movement measuring system 54 and used in the beam application 62, e.g. the gating or beam tracking, matches with the ion radiography results expected in this movement phase, the irradiation is continued. By contrast, when the ion radiography result exceeds predetermined threshold values of agreement with the expected ion radiography results, the beam application 62 is aborted or adapted by control device 39.

Figure 9:
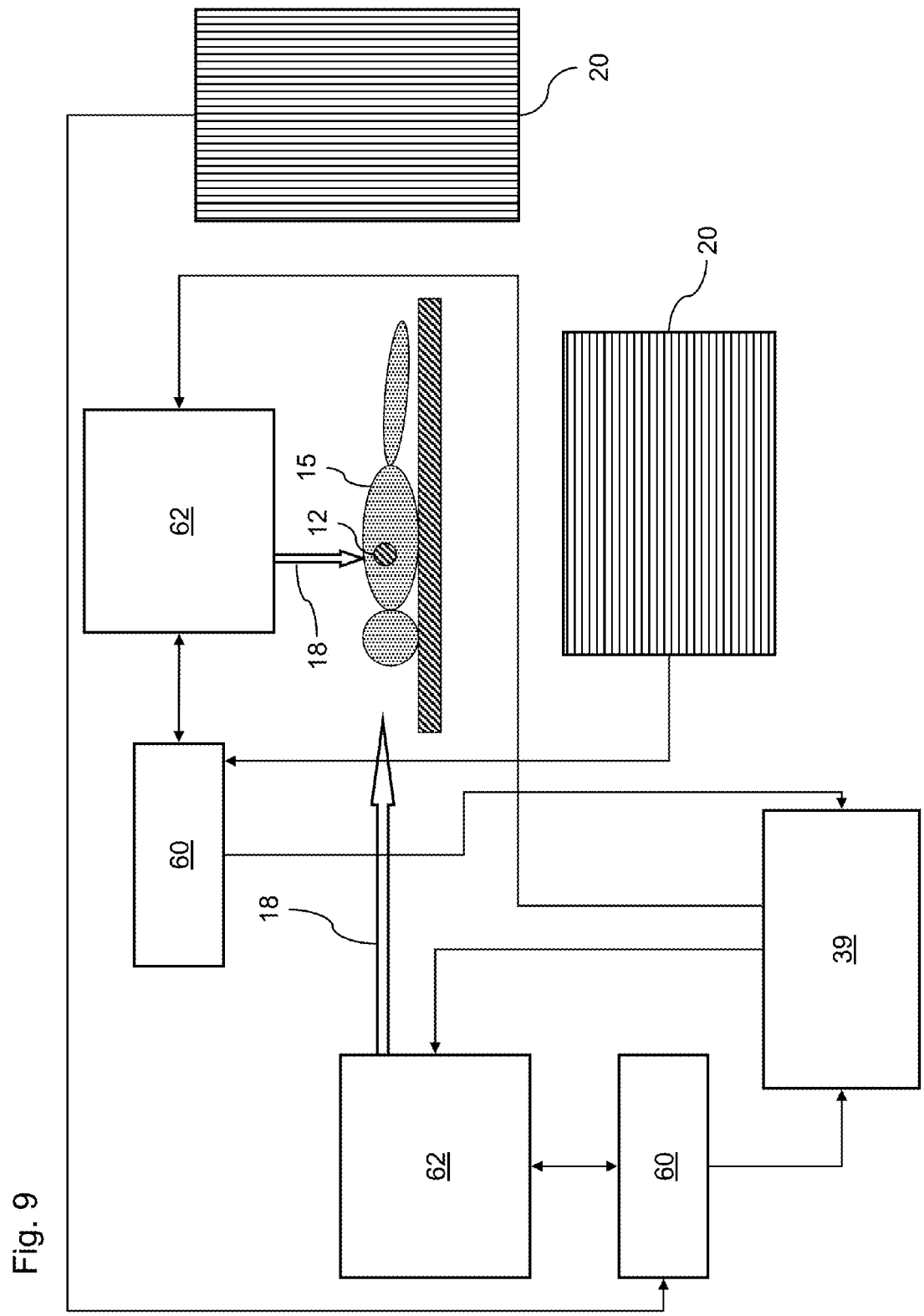
FIG. 9 is a schematic diagram illustrating the irradiation of a target volume from two different directions.

FIG. 9 shows an embodiment of the present disclosure, in which the target volume 12 or the patient 15 is irradiated with the ion beam 18 from two different directions. Accordingly, two ion radiography detectors 20 are provided for acquiring the ion radiographs. If, as in this example, irradiation with the ion beam 18 is performed from at least two different directions, ion radiographs from different directions will be available. The information obtained with the ion radiography measurements 60 from at least two different directions is superior to a purely two-dimensional information of a single radiograph, however, it is not a fully three-dimensional radiography information yet. Therefore, this type of irradiation is referred to as 2.5D radiography. In any case, the beam application 62 can be controlled selectively with the respective ion radiograph.

Figure 10:
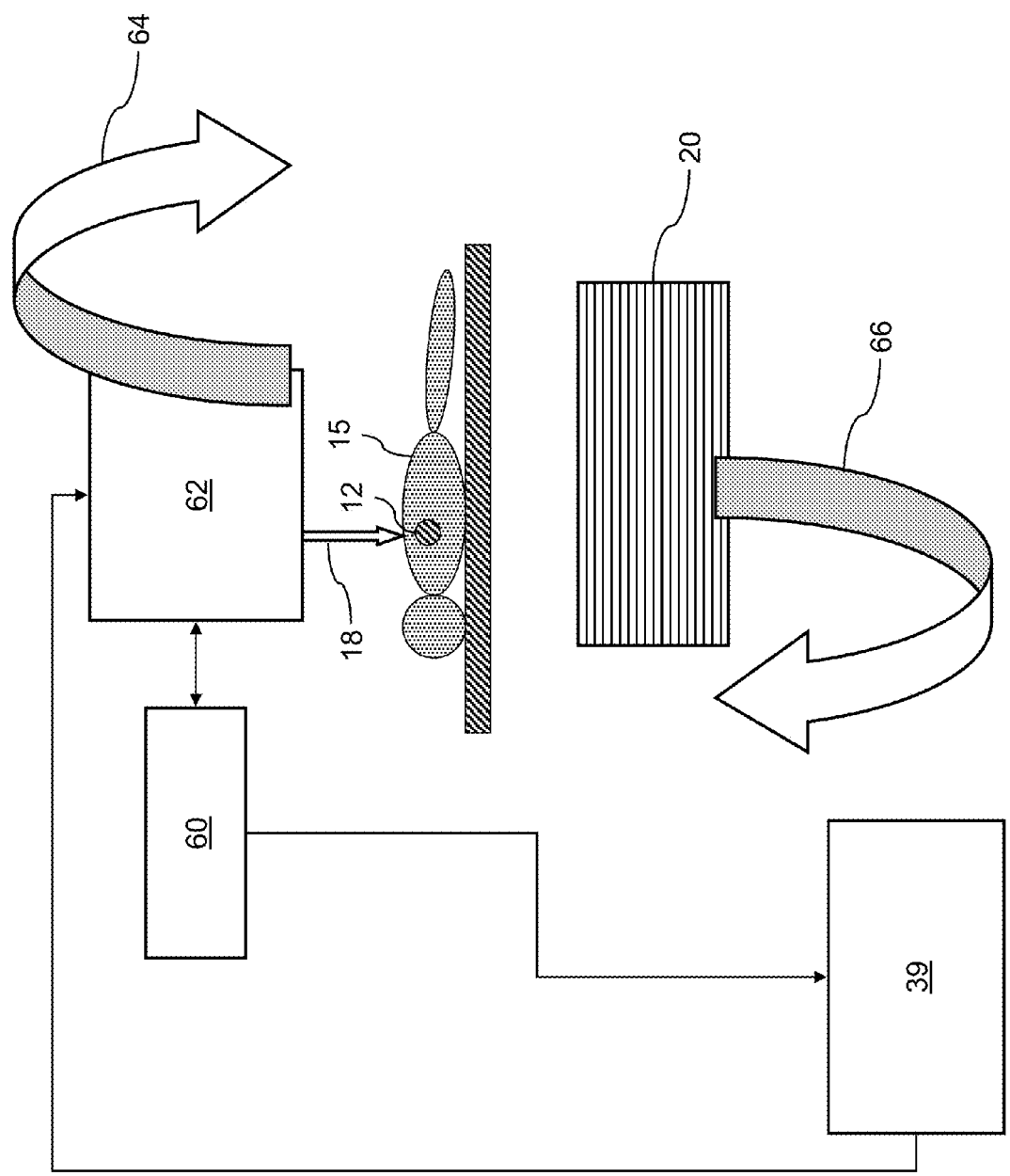
FIG. 10 is a schematic diagram illustrating the irradiation of a target volume using a rotating gantry.

FIG. 10 shows an embodiment with a rotating gantry, the rotation of beam application 62 being symbolized by arrow 64. The ion radiography detector 20 is co-rotated with the gantry (not shown) opposite to the beam application, which is symbolized by arrow 66. Similar to the so-called RapidArc method (photons), this permits to have the beam outlet and the ion radiography detector 20 rotating around the patient during the radiography irradiation, so that 3D ion radiographs can be acquired similar to an X-ray CT, but here additionally with the range information inherent to the ion radiograph.

Figure 11:
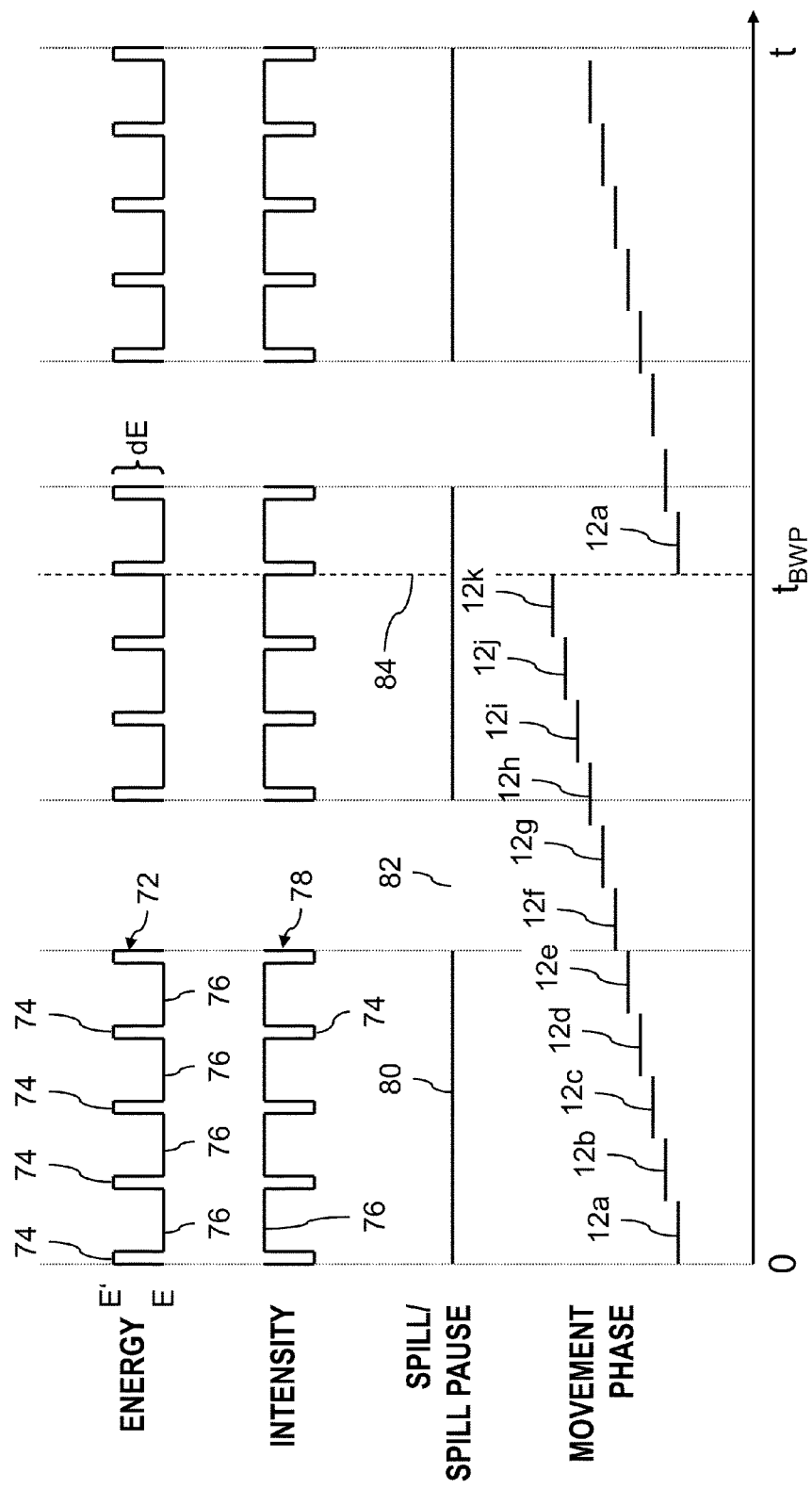
FIG. 11 illustrates the timing of the radiography phases and deposition phases according to one embodiment of the present disclosure.

FIG. 11 shows an exemplary embodiment of a time sequence of the radiography phases and deposition phases. The uppermost graph 72 shows the energy of the ion beam which is cyclically switch up and down between radiography phases 74 with higher radiography energy and deposition phases 76 with lower deposition energy. The intensity 78 of the ion beam is controlled inversely to the energy 72 of the ion beam, i.e. in the radiography phases 74 a lower intensity of the ion beam is applied than in the deposition phases 76. Therefore, the exposure dose is relatively low in the method of the present disclosure. The factor by which the ion beam intensity can be reduced during the radiography phase as compared to the deposition phase depends on the speed of the wobbling magnets and the characteristic of the radiography detector 20, for example. The slower the wobbling magnets and the ion radiography detector 20 are operating, the greater may usually be chosen the intensity reduction. In principle, a reduction in intensity during the radiography phase by a factor of 10 to 100 relative to the deposition phase appears to be possible.

In the example shown in FIG. 11, the cycle of alternation between the radiography phases and deposition phases is coordinated with the scanning of the target volume 12 by the scanning device 38 for deposition. For example, the change from deposition phase 76 to radiography phase 74 is effected when a predetermined number of grid points have been irradiated, e.g. after 100 grid points. Thus, the duration of deposition phase 76 corresponds to the duration for irradiating 100 grid points. The duration of the radiography phases 74 is selected considerably shorter than the duration of the deposition phases 76.

The illustrated example relates to an irradiation system 1 including a synchrotron 24'. A person skilled in the art will know that the ion beam is extracted discontinuously from a synchrotron, in so-called spills, the spills being denoted by 80 and the spill pauses by 82. The movement of the target volume 12 is divided into eleven movement phases 12a to 12k, extending in two spills in this example. The movement cycle 12a to 12k terminates at $t_{BWP}$ at dotted line 84, in this example, where a new movement cycle starts with the first movement phase 12a, etc. Insofar as the movement of target volume 12 refers to a patient's breathing, the movement cycle (breathing cycle) will typically have a duration of about 5 seconds.

Figure 12:
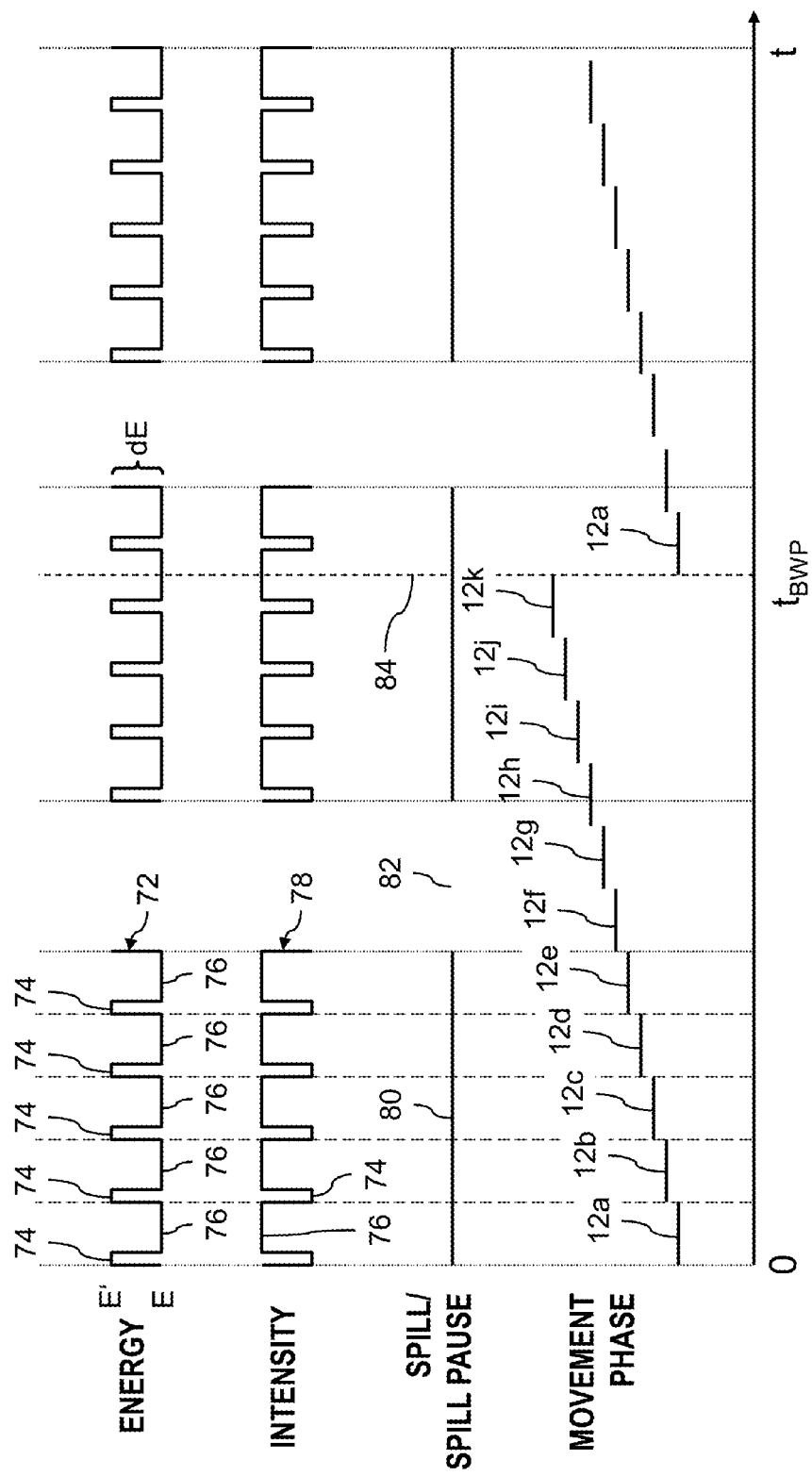
FIG. 12 illustrates the radiography phases and deposition phases according to another embodiment of the present disclosure.

FIG. 12 shows an alternative cycle of radiography phases 74 and deposition phases 76, in which the radiography-deposition cycle is matched with the movement phases 12a to 12k or is synchronized with the movement phases. The change from a deposition phase 76 to a radiography phase 74 coincides with the change from one movement phase to the next one. For this purpose, the cycle of radiography phases and deposition phases is triggered by the measurement of the movement measuring system 54 so that the change from the deposition phase 76 to the radiography phase 74 occurs when the movement measuring system 54 detects the change to the next phase of movement. Therefore, a separate radiography measurement is performed for each movement phase. Accordingly, the cycle of radiography phases and deposition phases is synchronized with the cycle of movement phases in this example. Referring to FIGS. 5 to 7, the synchronization is accomplished by means of controller device 39.

Figure 13:
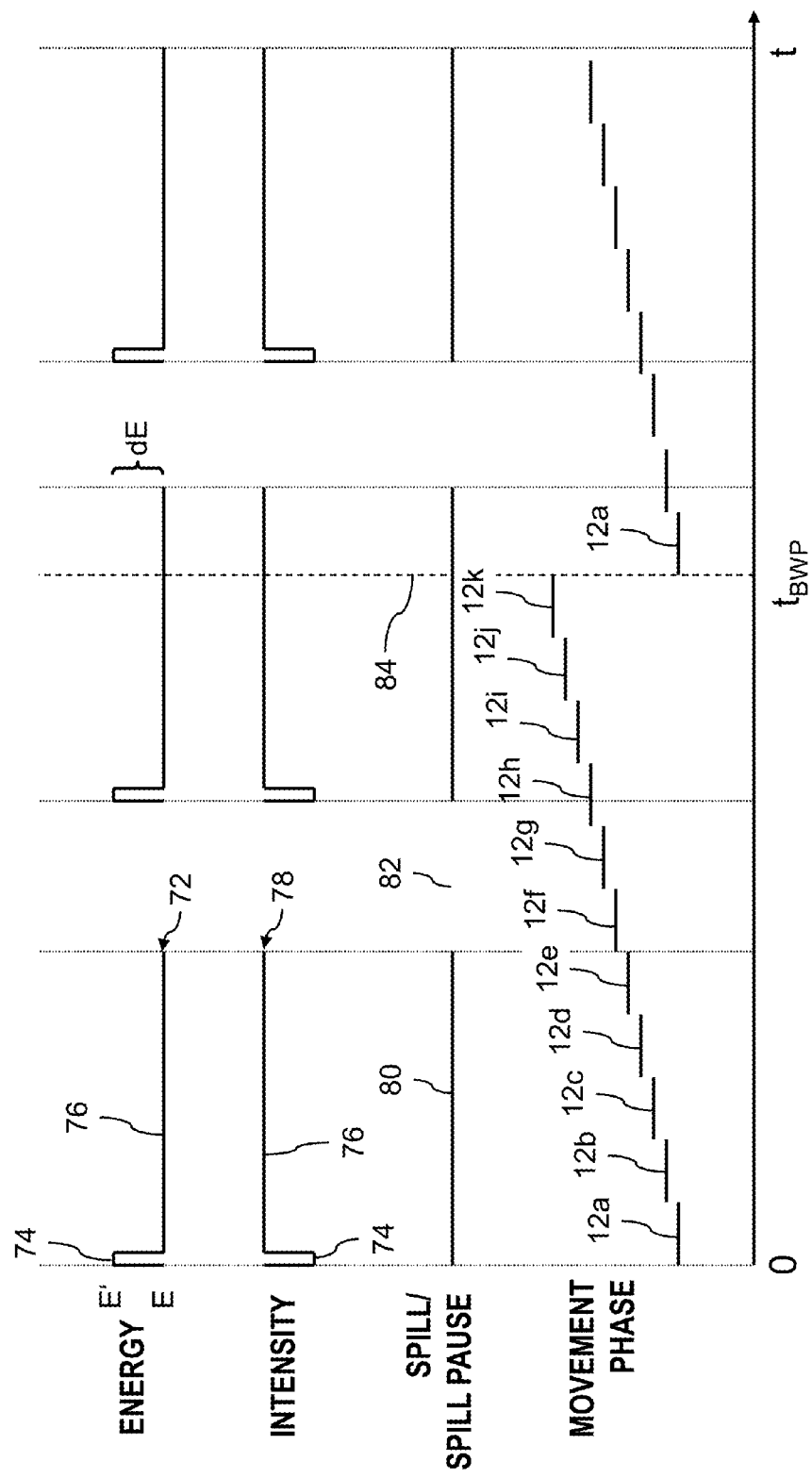
FIG. 13 illustrates the radiography phases and deposition phases according to yet another embodiment of the present disclosure.

Referring to FIG. 13, the cycle of radiography phases and deposition phases may as well be synchronized with the interval of beam extraction, i.e. with the duration of spill 80 in the example of the synchrotron 24'. In the present case this means that there will be a radiography phase at the beginning of each spill 80, and for the rest of the spill a dose is deposited in target volume 12.

Again, this synchronization may be accomplished using a suitably programmed controller device 39.

Figure 14:
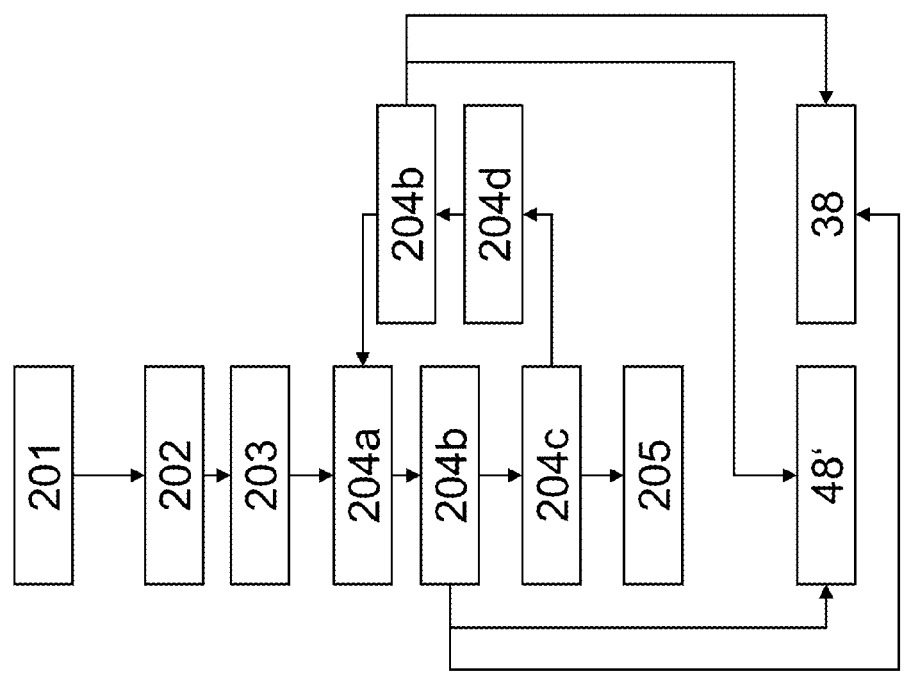
FIG. 14 is a flow chart of an irradiation according to one embodiment of the present disclosure.

FIG. 14 shows a flow chart for irradiation in the context of the present disclosure, with radiography phases and (optional) real time intensity control and (optional) wobbling using the scanning system 38.

In step 201, the irradiation therapy is prepared, which comprises diagnosis, imaging, and 4D irradiation planning etc., which is generally known to a person skilled in the art.

In step 202, the radiography parameters are defined, including the radiography energy E', the beam intensity 78 in the radiography phases 74, and/or the field size for the radiography measurement, and/or the frequency and time or cycle of the radiography measurements.

In step 203, a DRRM is calculated, for example by calculating the energy loss of the ion beam in the patient's body 15 with spatial resolution based on CT data and irradiation planning data (beam direction, energy etc.).

Step 204a defines a deposition phase 76 with the lower deposition energy E and the higher beam intensity 78, which in case of tumor therapy is a phase of therapeutic irradiation. As already described above, a deposition phase 76 may comprise the irradiation of a multiplicity of grid points.

In step 204b, the parameters of the irradiation system 1 are adjusted for the subsequent radiography measurement. This includes, by way of example, the variation of the beam energy 72 from the deposition energy E to the radiography energy E', for example using energy modulator 48, 48', and optionally the reduction of beam intensity 78. Both can be performed in real time.

In step 204c, the radiography measurement is performed, for example by wobbling the ion beam 18 across the entire internal target volume 14 (ITV). For this purpose, for example, scanner magnets 38a, 38b are driven appropriately by controller device 39. Depending on the result of the radiography measurement, irradiation is possibly aborted in step 205. Possibly even a new irradiation planning is done hereafter.

If the radiography measurement is within predetermined thresholds, the irradiation may be adapted in step 204d, if necessary. Then, in another step 204b, the irradiation system is reset to the deposition energy E, for example by introducing the energy modulator plate 48' into the beam path or by appropriately rotating the pie-shaped energy modulator 48, and by appropriately resuming the scanning process for dose deposition in the target volume, which is then again continued in step 204*a*.

Thus, the radiography measurement is used as a control parameter in control loop 204*a* to 204*d*.

When the entire irradiation plan has been processed, the irradiation is terminated, also in step 205. The adjustment of the irradiation parameters when changing from the radiography phase 74 to the deposition phase 76 and vice versa in steps 204*b* is accomplished here by appropriately driving the energy modulator 48', 48 and the scanning device 38 by controller device 39.

Figure 15:
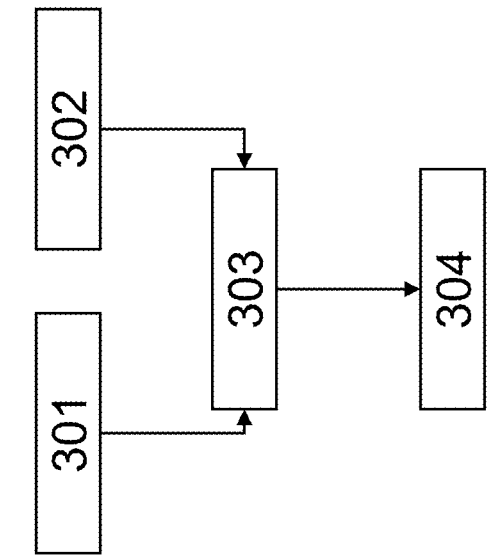
FIG. 15 is a flow chart of real-time evaluation with DRRM according to one embodiment of the present disclosure.

FIG. 15 shows a flow chart for combining the radiography measurement with the measurement results of the movement measuring system 54.

In step 301, the radiography measurement is performed using the ion radiography detector 20.

Simultaneously and independently thereof, in step 302, the movement of the target volume is detected, for example in form of a surrogate measurement, using the motion detection system 54.

In step 303, controller device 39 compares the ion radiography measurement with the expectation from the surrogate measurement and in response to the result of this comparison decides about the following procedure or a possible abortion of the irradiation.

In step 304, in case the irradiation is continued, the target volume is irradiated during a deposition phase 76.

Otherwise, the procedure corresponds to that of FIG. 14.

Figure 16:
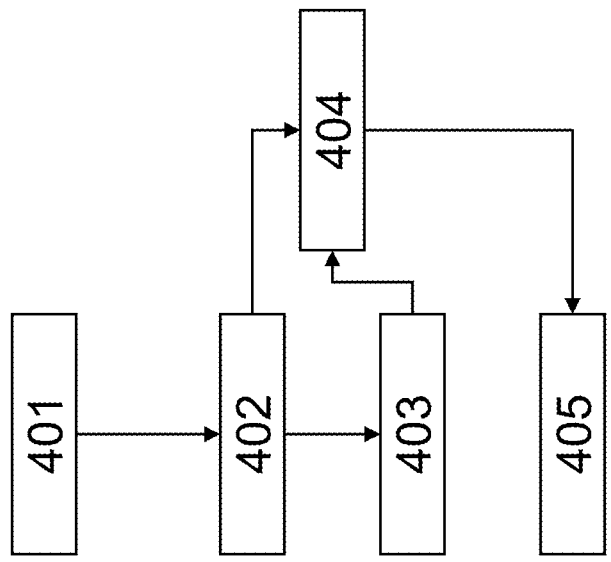
FIG. 16 is a flow chart of a combination of irradiation and surrogate measurement according to one embodiment of the present disclosure.

FIG. 16 shows a flow chart of a real time evaluation with DRRM.

In step 401, a DRRM is calculated for each 4D CT phase. This step is in particular performed prior to irradiation.

Box 402 symbolizes the DRRMs thus calculated.

In step 403, a radiography measurement is performed during a radiography phase 74.

In step 404, the result of the radiography measurement of step 403 is compared with the expectation of the precalculated DRRM 402, e.g. using controller device 39. Depending on the result of this comparison 404, the irradiation is adapted or aborted in step 405, as the case may be.

It will be apparent to those skilled in the art that the embodiments described above are given by way of example only and that the invention is not limited thereto, but rather may be varied in many ways without departing from the scope of the claims. Furthermore, it will be apparent that the features also define individually influential components of the present disclosure, irrespective of whether they are disclosed in the description, the claims, the figures, or otherwise, even if they are described together with other features.

The invention claimed is:

1. A method for irradiating a target volume with an ion beam;
    wherein the irradiation of the target volume is divided over time into at least one radiography phase and at least one deposition phase;
    wherein the energy of the ion beam is altered over time between the at least one radiography phase and the at least one deposition phase, such that
    i) in the at least one radiography phase, the range of the ion beam is distal with respect to the target volume, so that the ion beam passes through the target volume, and wherein by means of the ion beam an ion radiograph of the target volume is acquired by detecting the ion beam with an ion radiography detector that is arranged distal with respect to the target volume; and
    ii) in the at least one deposition phase, the range of the ion beam is within the target volume, so that the ion beam is stopped in the target volume to deposit a predetermined dose in the target volume,
    wherein in the at least one deposition phase, the intensity of the ion beam is set considerably higher than in the at least one radiography phase.

2. The method as claimed in claim 1,
    wherein the irradiation of the target volume is divided over time into a plurality of radiography phases and a plurality of deposition phases;
    wherein between the radiography phases and the deposition phases the energy of the ion beam is alternately switched up and down, so that in alternating cycles:
    i) in the radiography phases, the range of the ion beam is distal with respect to the target volume, so that the ion beam passes through the target volume, and wherein by means of the ion beam ion radiographs of the target volume are acquired by detecting the ion beam with an ion radiography detector that is arranged distal with respect to the target volume; and
    ii) in the deposition phases, the range of the ion beam is within the target volume, so that the ion beam is stopped in the target volume to deposit a respective predetermined dose in the target volume.

3. The method as claimed in claim 2,
    wherein in the deposition phases different isoenergy layers of the target volume are targeted with the ion beam to deposit a predetermined dose in the respective isoenergy layers, and wherein a radiography measurement according to i) is performed at least prior to the irradiation of each isoenergy layer for depositing a dose.

4. The method as claimed in claim 1,
    wherein in the at least one deposition phase the energy of the ion beam is reduced from the higher energy for radiography to the lower energy for deposition using a passive energy modulator.

5. The method as claimed in claim 1,
    wherein the target volume is a target volume that is cyclically moving during the irradiation, and the cyclical movement of the target volume is divided into a plurality of movement phases, and wherein the duration of the at least one radiography phase or the plurality of radiography phases is not greater than the duration of each of the movement phases.

6. A method for irradiating a target volume with an ion beam;
    wherein the irradiation of the target volume is divided over time into at least one radiography phase and at least one deposition phase;
    wherein the energy of the ion beam is altered over time between the at least one radiography phase and the at least one deposition phase, such that
    i) in the at least one radiography phase, the range of the ion beam is distal with respect to the target volume, so that the ion beam passes through the target volume, and wherein by means of the ion beam an ion radiograph of the target volume is acquired by detecting the ion beam with an ion radiography detector that is arranged distal with respect to the target volume; and
    ii) in the at least one deposition phase, the range of the ion beam is within the target volume, so that the ion beam is stopped in the target volume to deposit a predetermined dose in the target volume, wherein the movement of the target volume is compensated for by active ion beam tracking, and wherein the active ion beam tracking is controlled in response to the ion radiographs acquired by the ion radiography detector.

7. The method as claimed in claim 1,
wherein in the at least one radiography phase, a laterally two-dimensionally spatially resolved ion radiograph is acquired by passing the ion beam through a plurality of grid points of the target volume and determining the range of the ion beam after it has passed through the target volume for each of the grid points in the ion radiograph to create an at least two-dimensional map of the range of the ion beam.

8. The method as claimed in claim 1,
wherein the irradiation method is a scanning method and wherein in the at least one radiography phase, the ion beam is wobbled across at least a portion of the lateral area of the target volume.

9. The method as claimed in claim 8,
wherein in at least one of the plurality of deposition phases, the ion beam is scanned across the clinical target volume; and
wherein in the at least one the plurality of radiography phases, the ion beam is wobbled across at least a portion of the lateral area of the internal target volume beyond the clinical target volume.

10. The method as claimed in claim 1,
wherein a range simulation calculation is performed in order to calculate simulated target values for the range of the ion beam after it has passed through the target volume in the radiography phase;
wherein during irradiation in the radiography phase the actual range of the ion beam after having passed through the target volume is determined; and
wherein the determined actual ranges are compared with the simulated target values.

11. The method as claimed in claim 1,
wherein a range simulation calculation is performed for a plurality of grid points to create a multi-dimensional map of simulated target values of the range of the ion beam;
wherein during the irradiation in the radiography phase, the actual range of the ion beam after having passed through the target volume is determined for a plurality of grid points, and based thereon a multi-dimensional ion radiograph with the respective actual ranges of the ion beam is created; and
wherein the ion radiograph is compared with the map of simulated target values.

12. The method as claimed in claim 1,
wherein additionally the movement of the target volume or a movement surrogate is measured using an internal or external movement measuring system, and wherein the measurement results of the movement measuring system are automatically associated with the ion radiographs acquired using the ion radiography detector, and wherein the irradiation is controlled based on said associated data.

13. The method as claimed in claim 1,
wherein additionally the movement of the target volume or a movement surrogate is measured using an internal or external movement measuring system, and wherein the alternation between the at least one radiography phase and the at least one deposition phase is controlled in response to the measurement results of the movement measuring system.

14. A method for irradiating a target volume with an ion beam;
wherein the irradiation of the target volume is divided over time into at least one radiography phase and at least one deposition phase;
wherein the energy of the ion beam is altered over time between the at least one radiography phase and the at least one deposition phase, such that
i) in the at least one radiography phase, the range of the ion beam is distal with respect to the target volume, so that the ion beam passes through the target volume, and wherein by means of the ion beam an ion radiograph of the target volume is acquired by detecting the ion beam with an ion radiography detector that is arranged distal with respect to the target volume; and
ii) in the at least one deposition phase, the range of the ion beam is within that target volume, so that the ion beam is stopped in the target volume to deposit a predetermined dose in the target volume,
wherein in the at least one radiography phase, the target volume is irradiated from more than one direction thereby acquiring at least one ion radiograph with more than two spatial dimensions.

15. An irradiation system for irradiating a target volume with an ion beam, comprising:
an accelerator and beam guiding device for generating and accelerating an ion beam and for guiding and directing the ion beam to the target volume;
a controller device for controlling the irradiation;
a device for varying the energy of the ion beam over time, between at least one radiography phase and at least one deposition phase, by means of which
i) in the at least one radiography phase the energy of the ion beam is adjusted to a radiography energy having a range distal with respect to the target volume wherein the ion beam passes through the target volume;
ii) in the at least one deposition phase the energy of the ion beam is adjusted to a deposition energy having a range within the target volume, wherein the ion beam is stopped in the target volume in order to deposit a predetermined dose in the target volume;
an ion radiography detector arranged distal with respect to the target volume for acquiring ion radiographs of the target volume by detecting the ion beam that passes through the target volume in the radiography phase,
wherein said controller device is configured to control the irradiation system in a manner so that in the at least one deposition phase the intensity of the ion beam is set to be considerably higher than in the at least one radiography phase.

16. The irradiation system as claimed in claim 15,
wherein the device for varying the energy of the ion beam over time switches up and down the energy of the ion beam in an alternating sequence that includes a plurality of radiography phases and a plurality of deposition phases, such that in cyclically alternating manner:
i) in each of the radiography phases the energy of the ion beam is adjusted to the radiography energy, with a range distal with respect to the target volume, wherein the ion beam passes through the target volume;
ii) in the deposition phases the energy of the ion beam is adjusted to the deposition energy, with a range within the target volume, wherein the ion beam is stopped in the target volume to deposit a respective predetermined dose in the target volume.

17. The irradiation system as claimed in claim 16,
wherein said controller device is configured to control the irradiation system so that:
in the deposition phases different isoenergy layers of the target volume are approached with the ion beam to deposit a respective predetermined dose in the isoenergy layers; and
wherein a radiography measurement is performed using the ion radiography detector at least prior to the irradiation of each isoenergy layer for depositing a dose.

18. The irradiation system as claimed in claim 15, wherein the device for varying the energy of the ion beam over time comprises a passive energy modulator which in the at least one deposition phase reduces the energy of the ion beam from the higher radiography energy to the lower deposition energy.

19. The irradiation system as claimed in claim 15, comprising means for dividing the movement of a target volume that is cyclically moving during the irradiation into a plurality of movement phases, wherein the duration of the at least one radiography phase is not greater than the duration of each of the movement phases.

20. An irradiation system for irradiating a target volume with an ion beam, by way of example using a method for irradiating a target volume with an ion beam;
wherein the irradiation of the target volume is divided over time into at least one radiography phase and at least one deposition phase;
wherein the energy of the ion beam is altered over time between the at least one radiography phase and the at least one deposition phase, such that
i) in the at least one radiography phase, the range of the ion beam is distal with respect to the target volume, so that the ion beam passes through the target volume, and wherein by means of the ion beam an ion radiograph of the target volume is acquired by detecting the ion beam with an ion radiography detector that is arranged distal with respect to the target volume; and
ii) in the at least one deposition phase, the range of the ion beam is within the target volume, so that the ion beam is stopped in the target volume to deposit a predetermined dose in the target volume,
wherein they system comprises:
a device for compensating the movement of the target volume by active ion beam tracking, wherein the controller device is adapted to control the active ion beam tracking in response to the ion radiographs acquired by the ion radiography detector.

21. The irradiation system as claimed in claim 15, wherein the ion radiography detector is a spatially resolving detector which acquires a respective laterally two-dimensionally spatially resolved ion radiograph in the at least one radiography phase by having the ion beam passing through a plurality of grid points of the target volume;
further comprising a computing device for determining the range of the ion beam after it has passed through the target volume for each of said grid points in the ion radiographs and for creating an at least two-dimensional map of the range of the ion beam after having passed through the target volume.

22. The irradiation system as claimed in claim 15,
wherein the system comprises a scanning device for scanning the ion beam across the target volume, wherein the controller device is adapted to control the scanning device so that
in the at least one deposition phase, the ion beam is scanned across the target volume to deposit a dose; and
in the at least one radiography phase, the ion beam is wobbled across at least a portion of the lateral area of the target volume.

23. The irradiation system as claimed in claim 22,
wherein the controller device is adapted to control the scanning device so that in the at least one deposition phase, the ion beam is scanned across the clinical target volume, and in the at least one radiography phase the ion beam is wobbled across at least a portion of the lateral area of the internal target volume beyond the clinical target volume.

24. The irradiation system as claimed in claim 15,
wherein the system comprises computing device, configured to:
perform a range simulation calculation in order to calculate simulated target values for the range of the ion beam after it has passed through the target volume in the at least one radiography phase;
determine the actual range of the ion beam after it has passed through the target volume in the at least one radiography phase in response to the measured values of the ion radiography detector; and
compare the determined actual ranges with the simulated target values.

25. The irradiation system as claimed in claim 15,
wherein the system comprises a computing device, configured to:
perform a range simulation calculation for a plurality of grid points to create a multi-dimensional map of simulated target values of the range of the ion beam after it has passed through the target volume in the radiography phase;
determine the actual ranges of the ion beam after it has passed through the target volume for a plurality of grid points, and to create a multi-dimensional ion radiograph with the respective actual ranges of the ion beam; and
compare the ion radiograph with the map of simulated target values.

26. The irradiation system as claimed in claim 15,
wherein the system comprises an internal or external movement measuring system for measuring the movement of the target volume or of a movement surrogate, and wherein the controller device is configured to:
receive measurement results of the movement measuring system;
receive ion radiographs of the ion radiography detector; and
automatically associate the measurement results and the ion radiographs and to control the irradiation in response to the associated data.

27. The irradiation system as claimed in claim 15,
wherein the system comprises an internal or external movement measuring system for measuring the movement of the target volume or of a movement surrogate, and wherein the controller device is configured to:
control the alternation between in the at least one radiography phase and the at least one deposition phase in response to the measurement results of the movement measuring system.

28. An irradiation system for irradiating a target volume with an ion beam, by way of the example using a method for irradiating a target volume with an ion beam;
wherein the irradiation of the target volume is divided over time into at least one radiography phase and at least one deposition phase;

wherein the energy of the ion beam is altered over time between the at least one radiography phase and the at least one deposition phase, such that
i) in the at least one radiography phase, the range of the ion beam is distal with respect to the target volume, so that the ion beam passes through the target volume, and wherein by means of the ion beam an ion radiograph of the target volume is acquired by detecting the ion beam with an ion radiography detector that is arranged distal with respect to the target volume; and
ii) in the at least one deposition phase, the range of the ion beam is within the target volume, so that the ion beam is stopped in the target volume to deposit a predetermined dose in the target volume, wherein the irradiation system is configured to irradiate the target volume from more than one direction in the at least one radiography phase to thereby acquire at least one ion radiograph with more than two spatial dimensions.

\* \* \* \* \*